(12) United States Patent
Fritchie et al.

(10) Patent No.: US 8,691,149 B2
(45) Date of Patent: Apr. 8, 2014

(54) SYSTEM FOR AUTOMATICALLY LOADING IMMUNOASSAY ANALYZER

(75) Inventors: Patrick P. Fritchie, Southlake, TX (US); Gregory E. Gardner, Grapevine, TX (US); Richard W. Mahoney, Grapevine, TX (US)

(73) Assignee: Abbott Laboratories, Abbott Park, IL (US)

( * ) Notice: Subject to any disclaimer, the term of this patent is extended or adjusted under 35 U.S.C. 154(b) by 483 days.

(21) Appl. No.: 12/257,428

(22) Filed: Oct. 24, 2008

(65) Prior Publication Data
US 2009/0117004 A1    May 7, 2009

Related U.S. Application Data

(60) Provisional application No. 60/985,794, filed on Nov. 6, 2007.

(51) Int. Cl.
*G01N 35/10* (2006.01)
*B01L 3/02* (2006.01)
*B03C 1/28* (2006.01)
*G01N 35/04* (2006.01)

(52) U.S. Cl.
CPC .............. *B01L 3/0289* (2013.01); *B03C 1/284* (2013.01); *G01N 35/1074* (2013.01); *B01L 2400/043* (2013.01); *G01N 2035/0422* (2013.01)
USPC ................ 422/65; 422/63; 210/695; 210/222

(58) Field of Classification Search
None
See application file for complete search history.

(56) References Cited

U.S. PATENT DOCUMENTS

| | | | |
|---|---|---|---|
| 5,082,631 A * | 1/1992 | Lenmark et al. | 422/551 |
| 5,578,270 A * | 11/1996 | Reichler et al. | 422/67 |
| 5,604,130 A * | 2/1997 | Warner et al. | 435/286.7 |
| 5,795,784 A | 8/1998 | Arnquist et al. | |
| 5,856,194 A | 1/1999 | Arnquist et al. | |
| 6,040,192 A * | 3/2000 | Tuunanen | 436/177 |
| 6,277,332 B1 * | 8/2001 | Sucholeiki | 422/128 |
| 6,353,774 B1 | 3/2002 | Goldenberg et al. | |
| 6,448,092 B1 | 9/2002 | Tuunanen | |

(Continued)

FOREIGN PATENT DOCUMENTS

| | | | |
|---|---|---|---|
| WO | 00/45164 A1 | | 8/2000 |
| WO | WO-2005/044460 | * | 5/2005 |
| WO | 2005059929 A2 | | 6/2005 |

OTHER PUBLICATIONS

Fang, et al., Automation of Nucleic Acid Isolation on KingFisher Magnetic Particle Processors, XP-002517862, Copyright © 2007 by The Association for Laboratory Automation doi:10.1016/j.jala.2007.05.001, pp. 195-201.

(Continued)

*Primary Examiner* — P. Kathryn Wright
(74) *Attorney, Agent, or Firm* — Hanley, Flight & Zimmerman, LLC

(57) ABSTRACT

A component of a laboratory automation system that integrates (a) separating a solid magnetic substrate from the liquid contents of a reaction vessel, (b) management of the thermal characteristics of the component of the laboratory automation system, (c) automated loading of multi-well plates and tip combs into the component of the laboratory automation system, (d) automated unloading of multi-well plates and tip combs from the component of the laboratory automation system, and (e) reading of radio frequency identification tags attached to multi-well plates.

20 Claims, 21 Drawing Sheets

(56) References Cited

U.S. PATENT DOCUMENTS

| | | | |
|---|---|---|---|
| 6,596,162 | B2 | 7/2003 | Tuunanen |
| 6,691,748 | B1* | 2/2004 | Tajima ........................ 141/130 |
| 7,033,543 | B1 | 4/2006 | Panzer et al. |
| 2001/0048899 | A1* | 12/2001 | Marouiss et al. ............. 422/100 |
| 2005/0220675 | A1* | 10/2005 | Reed et al. .................... 422/100 |
| 2005/0247782 | A1* | 11/2005 | Ambartsoumian ........... 235/385 |
| 2006/0121602 | A1* | 6/2006 | Hoshizaki et al. ......... 435/288.7 |
| 2006/0210435 | A1* | 9/2006 | Alavie et al. .................... 422/65 |
| 2007/0077648 | A1* | 4/2007 | Okamoto et al. .......... 435/303.1 |
| 2008/0024301 | A1 | 1/2008 | Fritchie et al. |
| 2008/0118967 | A1 | 5/2008 | Korpela et al. |
| 2009/0117620 | A1 | 5/2009 | Frtichie et al. |
| 2009/0130745 | A1* | 5/2009 | Williams et al. ........... 435/287.2 |

OTHER PUBLICATIONS

KingFisher™ Micro-well User Manual, Revision 1.0, Apr. 9, 1999, Catalog No. 1507730, 18 pages.

KingFisher™ Software User Manual, Revision 1.0, Nov. 2001, Catalog No. 1508540, pp. 1-38.

KingFisher™ mL User Manual, Revision 1.0, Feb. 2002, Catalog No. 1508260, pp. 8-13.

Molecular Devices. SpectraMax [online], [retrieved on May 6, 2009]. Retrieved from the Internet: <URL: http:/www.moleculardevices.com/pages/instruments/spectramax_m5.html>, pp. 1-7.

PCT International Application No. PCT/US2008/081497, Notification of Transmittal of The International Search Report and The Written Opinion of The International Searching Authority, or The Declaration, Mailed: Mar. 23, 2009.

Polymerase chain reaction—Wikipedia, the free encyclopedia [online], [retrieved on Apr. 17, 2009]. Retrieved from the Internet: <URL: http:/en.wikipedia.org/wiki/Polymerase_chain_reaction>, pp. 1-13.

The KingFisher Family. Brochure [online]. Thermo Electron Corporation, 2006. [retrieved on Oct. 25, 2007]. Retrieved from the Internet: <URL: http://www.thermo.com/eThermo/CMA/PDFs/Various/File_31157.pdf>, pp. 1-6.

Thermal cycler—Wikipedia, the free encyclopedia [online], [retrieved on Apr. 17, 2009]. Retrieved from the Internet: <URL: http://en.wikipedia.org/wiki/Thermocycler>, p. 1.

Thermo Scientific. KingFisher Flex purification automate—Thermo Scientific [online], [retrieved on Apr. 17, 2009]. Retrieved from the Internet: <URL: http://www.thermo.com/com/cda/product/detail/1,,10136240,00.html>, pp. 1-3.

* cited by examiner

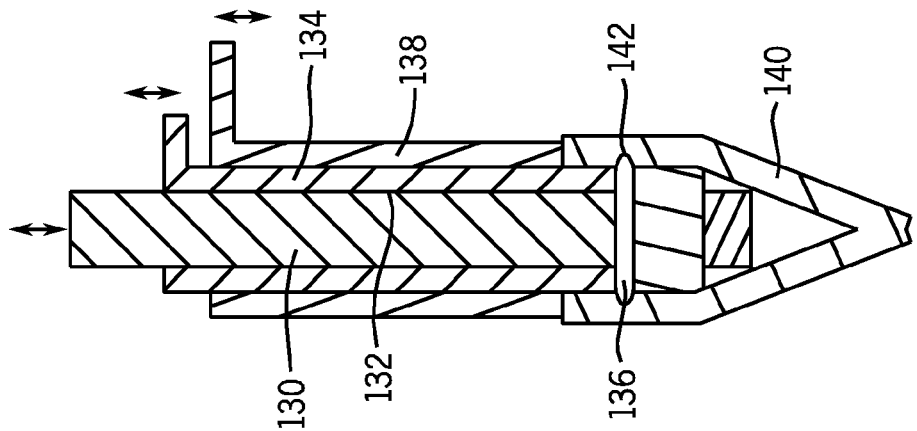
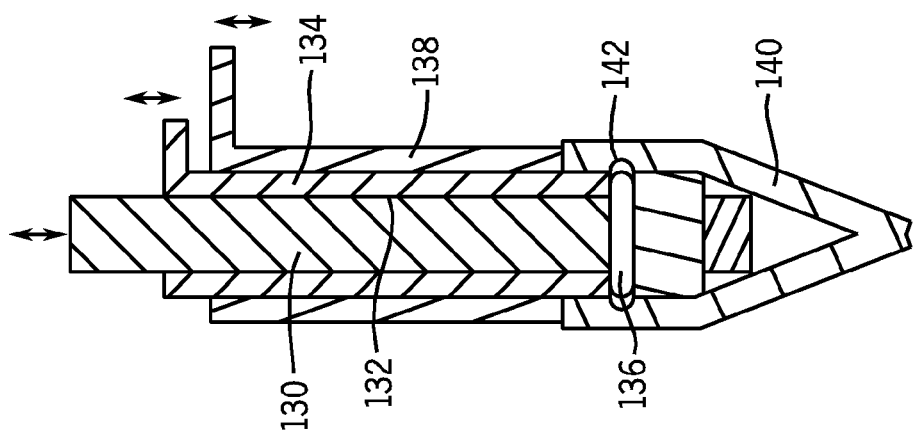
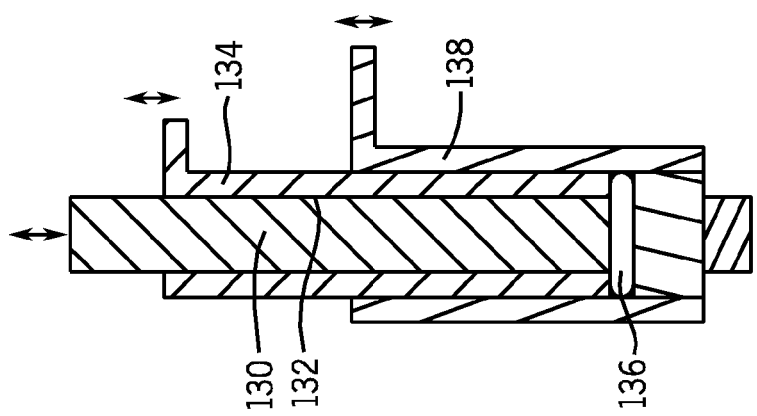
FIG. 20A
FIG. 20B
FIG. 20C ial Application Ser. No. 60/985,794, filed Nov. 6, 2007. -->

SYSTEM FOR AUTOMATICALLY LOADING IMMUNOASSAY ANALYZER

This application claims priority from U.S. Provisional Application Ser. No. 60/985,794, filed Nov. 6, 2007.

BACKGROUND OF THE INVENTION

1. Field of the Invention

This invention relates to diagnostic analyzers, and more particularly, to automated diagnostic analyzers.

2. Discussion of the Art

Automated analyzers are well-known in the field of clinical chemistry and in the field of immunochemistry. Representative examples of such automated analyzers include, but are not limited to, PRISM® analyzers, AxSYM® analyzers, ARCHITECT® analyzers, all of which are commercially available from Abbott Laboratories, Cobas® 6000, commercially available from Roche Diagnostics, Advia, commercially available from Siemens AG, Dimension Vista, commercially available from Dade Behring Inc., Unicel® DxC600i, commercially available from Beckman Coulter Inc., and VITROS, commercially available from Ortho-Clinical Diagnostics. Each of these analyzers suffers from various shortcomings, some more than others. Some of the shortcomings encountered by more than one of these automated analyzers include the use of large volumes of sample, the use of large volumes of reagents, the generation of large volumes of liquid waste, and high costs. Some of the aforementioned automated analyzers require a great deal of maintenance, both scheduled and unscheduled. In addition, some of the aforementioned automated analyzers have scheduling protocols for assays that cannot be varied, i.e., the assay scheduling protocols are fixed, which limits such features as throughput.

Users of automated clinical analyzers desire to automate as many functions as possible. In the area of automated immunoassays, some of which require separation of reaction products from a reaction mixture in a reaction vessel, certain types of subsystems are necessary for separating a solid magnetic substrate from the liquid contents of a reaction vessel. These liquid contents can be unbound sample, unbound conjugate, wash buffer, a pre-trigger solution. Some automated immunoassay analyzers do not have the necessary versatility that would enable them to be used in systems that are designed to allow seamless integration with clinical chemistry analyzers. For example, magnetic separation of solid magnetic substrate from the liquid contents of a reaction vessel is difficult to integrate with clinical chemistry assays because of the need to use external magnets, washing mechanisms, in-track vortexers, inflexible process paths, and instantaneous dispensing of liquids at certain key points of immunoassay protocols.

Commercially available subsystems for separating a solid magnetic substrate from the liquid contents of a reaction vessel that do not have (a) an incubation capability integrated with such separating capability, (b) an automated interface for loading reaction vessels, and (c) radio frequency reading of radio frequency identification tags attached to reaction vessels are difficult to operate efficiently.

Magnetic separation of a solid magnetic substrate from the liquid contents of a reaction vessel can be carried out by a method known as inverse magnetic particle processing. The operating principle of inverse magnetic particle processing technology, commonly referred to as MPP, involves moving magnetic particles from one micro-well to another micro-well, e.g., from a micro-well in a given row and column of a micro-well plate to a micro-well in the same row and in another column of the micro-well plate, at least one micro-well in the micro-well plate containing reagent(s) required for the immunoassay, rather than moving liquids from one micro-well to another micro-well. This principle stands in contrast to the external magnet method, which is used in such automated analyzers as the ARCHITECT® analyzer, commercially available from Abbott Laboratories. According to inverse magnetic particle processing technology, magnetic particles are transferred with the aid of the magnetic rods covered with disposable, specially designed plastic tip combs.

A magnetic particle processor commercially available under the trademarks KingFisher™, KingFisher™ 96, and KingFisher™ Flex does not have accessories that enable the incubation of a reaction mixture. In addition, the KingFisher™ magnetic particle processor and KingFisher™ 96 magnetic particle processor do not have an interface whereby micro-well plates and plastic tip combs can be automatically inserted into an area in which incubation of a reaction mixture can be carried out. Furthermore, the KingFisher™ magnetic particle processor and KingFisher™ 96 magnetic particle processor for separating a solid magnetic substrate from the liquid contents of a reaction vessel lack incubation capabilities, with the result that these apparatus do not readily accommodate immunoassay protocols. Still further, the KingFisher™ magnetic particle processor and KingFisher™ 96 magnetic particle processor do not have an interface that can read radio frequency identification tags attached to micro-well plates.

Accordingly, it would be desirable to develop an automated immunoassay analyzer that not only separates a solid magnetic substrate from the liquid contents of a reaction vessel but also has the capability for incubation of reaction mixtures. It would be further desirable to develop an automated immunoassay analyzer that enables the automatic insertion and removal of reaction vessels into and out of a magnetic particle processor. It would be further desirable to develop an automated immunoassay analyzer that enables chain of custody tracking of micro-well plates by means of radio frequency identification tags.

SUMMARY OF THE INVENTION

This invention provides an automated immunoassay analyzer that integrates (a) separating a solid magnetic substrate from the liquid contents of a reaction vessel, (b) management of the thermal characteristics of the immunoassay analyzer, (c) automated loading of micro-well plates and tip combs into the immunoassay analyzer, (d) automated unloading of micro-well plates and tip combs from the immunoassay analyzer, and (e) reading of radio frequency identification tags attached to micro-well plates.

In one aspect, this invention provides an apparatus and method for separating a solid magnetic substrate from the liquid contents of a reaction vessel in an immunoassay. These liquid contents can be unbound sample, unbound conjugate, wash buffer, pre-trigger solution. The apparatus comprises a conventional KingFisher™ magnetic particle processor or a conventional KingFisher™ 96 magnetic particle processor that have been modified to incorporate a resistive temperature detector for sensing the temperature of the magnetic particle processor and a heater pad for heating the contents of the micro-wells of a micro-well plate. The apparatus utilizes insulation, heater pads, and a controller to enable the incubation function to be integrated with the magnetic separation function.

In another aspect, this invention provides a system for (a) automating the loading of micro-well plates into a magnetic particle processor, (b) automating the loading of supplies for inverse magnetic particle processing procedures into a magnetic particle processor, and (c) dispensing of liquids into a system for the separation of solid magnetic substrate from the liquid contents of a reaction vessel, i.e., a micro-well in a micro-well plate.

In another aspect, this invention provides a system for automating the chain of custody tracking and a verification of geometric orientation of micro-well plates into a magnetic particle processor by providing an antenna inside of the magnetic particle processor to read radio frequency identification tags attached to micro-well plates.

In still another aspect, this invention can be adapted for use with any assay that involves separation of magnetic particles from the other components of a mixture. Such assays, include, but are not limited to, assays that involve extraction of nucleic acid(s) from samples. In other words, the use of the apparatus described herein is not limited to immunoassays.

The system comprises a movable interface, which enables access to a XYZ aspirating/dispensing device. The movable interface allows loading of micro-well plates into a magnetic particle processor and unloading of micro-well plates from the magnetic particle processor without the intervention of a human operator. In one embodiment, the movable interface comprises a tray for holding at least one micro-well plate, typically two micro-well plates. The tray can be driven out of the magnetic particle processor to enable the loading of the at least one micro-well plate. The tray can be driven into the magnetic particle processor to enable the mixing of samples with reagent(s) and separating a solid magnetic substrate from the liquid contents of a reaction vessel. The movable interface enables the loading of critical supplies for inverse magnetic particle processing procedures and the removal of these critical supplies after use without the intervention of a human operator. The aforementioned movable interface enables the dispensing of liquid between steps of magnetic separation of a solid magnetic substrate from the liquid contents of a reaction vessel. In another embodiment, the movable interface comprises a turntable for holding a plurality of micro-well plates. The turntable can be rotated to enable loading of the plurality of micro-well plates. The turntable can be driven into the magnetic particle processor to enable the mixing of samples with reagent(s) and separating a solid magnetic substrate from the liquid contents of a reaction vessel. The movable interface enables the loading of critical supplies for inverse magnetic particle processing procedures and the removal of these critical supplies after use without the intervention of a human operator.

The system combines magnetic separation, mixing, and washing functions with incubation functions, thereby providing a method for performing inverse magnetic particle processing protocols for immunoassays more effectively. The system allows automated immunoassay analyzers to be smaller, more reliable, and less complex than existing automated immunoassay analyzers, by combining two or more functions, by performing assays within a micro-well plate, and by using a XYZ aspirating/dispensing device to load micro-well plates into the magnetic particle processor. Elimination of washing mechanisms, pumps for washing mechanisms, in-track vortexers, process paths, reaction vessel loaders, and the requirement of instantaneous reagent addition is brought about by using micro-well plates rather than the consumable items utilized by conventional automated immunoassay analyzers. The system described herein allows new assay protocols to be accommodated with minimal effect upon the design of the automated immunoassay analyzer by using a XYZ aspirating/dispensing device to automatically obtain access to micro-well plates for dispensing of liquids into micro-wells. The required control synchronization can be performed via a commercially available interface on the magnetic particle processor, and a commercially available interface on the XYZ aspirating/dispensing device.

This invention provides an antenna inside the magnetic particle processor to read radio frequency identification tags attached to micro-well plates. This feature enables the verification of geometric orientation for a particular micro-well plate and chain of custody tracking of micro-well plates.

BRIEF DESCRIPTION OF THE DRAWINGS

FIG. 11A shows a top plan view of a supporting tray. FIG. 11B shows a top plan view of the supporting tray of FIG. 11A with a micro-well plate placed thereon. FIG. 11C shows a top plan view of the supporting tray of FIG. 11B with the micro-well plate pushed into position for a magnetic particle processing operation.

FIGS. 20A, 20B, 20C, 20D, and 20E are schematic diagrams illustrating the steps required to insert a gripping device or a pipette tip onto the end of a pipette and to remove the gripping device or the pipette tip from the end of the pipette.

DETAILED DESCRIPTION

Figure 1:
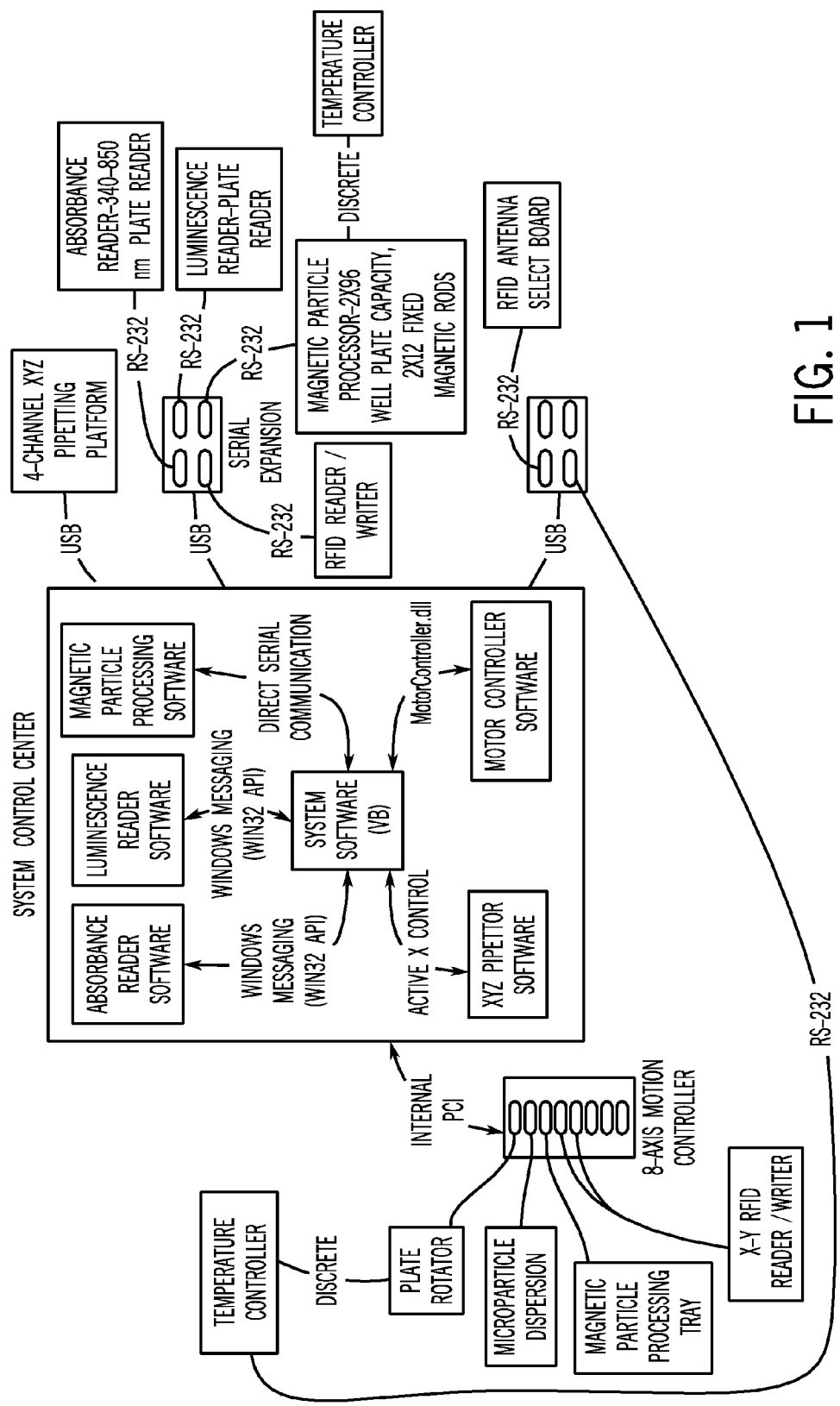
FIG. 1 is a schematic view of a computer interface suitable for providing control synchronization for the apparatus and method described herein.

As used herein, the term "immunoassay" means a biochemical test that measures the concentration of a substance in a biological liquid, typically serum, using the reaction of an antibody or antibodies to its (their) antigen. An immunoassay takes advantage of the specific binding of an antibody to its antigen. As used herein, a "chemiluminescent microparticle immunoassay", alternatively referred to as "chemiluminescent magnetic immunoassay", involves a chemiluminescent label conjugated to the antibody or the antigen. In this assay, a magnetic microparticle is coated with antibodies. The assay is intended to look for antigens in the sample. A second antibody is labeled with a chemiluminescent label. This second antibody is not attached to a magnetic microparticle. The antibody and antigen with attach in the following order: antibody on magnetic microparticle-antigen-antibody-chemiluminescent label. The magnetic microparticle is then washed off. The amount of antibody-antigen-enzyme is measured by adding pre-trigger solution and trigger solution and measuring the light produced. This type of immunoassay produces light when combined with its substrate, i.e., a specific binding member. The chemiluminescent reaction offers high sensitivity and ease of measurement. This type of immunoassay involves a noncompetitive sandwich format that yields results that are directly proportional to the amount of analyte present in the sample. As used herein, the term "magnetic" means paramagnetic.

As used herein, the term "sample", the expression "biological sample", and the like, mean a material suspected of containing an analyte. The sample can be used directly as obtained from the source in an assay or following a pretreatment to modify the character of the sample before undergoing an assay. The sample can be derived from any biological source, such as, for example, a physiological fluid, including, but not limited to, blood, saliva, ocular lens fluid, cerebral spinal fluid, sweat, urine, milk, ascites fluid, mucous, synovial fluid, peritoneal fluid, amniotic fluid, or the like. The sample can be pretreated prior to use, such as, for example, preparing plasma from blood, diluting viscous fluids, or the like. Methods of pretreatment can involve filtration, distillation, concentration, inactivation of interfering components, and the addition of reagents. Besides physiological fluids, other liquid samples can be used, such as, for example, water, food products, and the like. In addition a solid material suspected of containing the analyte can be used as the sample. As used herein, the term "analyte" refers to the compound or composition to be detected or measured.

As used herein, the expression "radio frequency identification" means is a generic term for technologies that use radio waves to automatically identify objects, such as, for example, containers for biological samples and containers for reagents for analyzing biological samples. The most common method of identification is to store a serial number that identifies the object, and perhaps other information relating to the object or contents thereof, on a microchip that is attached to an antenna. The microchip and the antenna together are called a radio frequency identification transponder or a radio frequency identification tag. The antenna enables the microchip to transmit the identification information and other information to a radio frequency identification reader. The radio frequency identification reader converts the radio waves reflected back from the radio frequency identification tag into digital information that can then be passed on to computers that can make use of it.

As used herein, the expression "aspirating/dispensing device" means a device that has the dual functions of removing liquids from containers by suction and distributing portions of the liquids aspirated into containers, e.g., micro-wells of micro-well plates. An aspirating/dispensing device that is capable of being used for the system described herein is described in U.S. Pat. No. 7,033,543, incorporated herein by reference. As used herein, the term "pipette", also called "pipet", "pipettor", means a laboratory instrument used to transport a measured volume of liquid. As used herein, the expression "micro-well plate", also called "microtiter plate", "microplate", means a flat plate having a plurality of "micro-wells" used as small test tubes. As used herein, the term "XYZ" refers to a device that can move in three directions, a first horizontal direction, a second horizontal direction that is perpendicular to the first horizontal direction, and a third direction that is perpendicular to both the first horizontal direction and the second horizontal direction.

As used herein, the expression "extraction of nucleic acid(s)" and the like, means removal of nucleic acid(s) from a sample. As used herein, the expression "amplification of nucleic acid(s)", and the like, refers to assays that use purified enzymes to isolate and then replicate specific nucleic acid(s) to levels it (they) can be detected. An example of a technique for amplification of nucleic acid(s) is polymerase chain reaction (PCR). As used herein, the expression "multi-well plate" means a plastic tray having an upper surface and a lower surface and a plurality wells depending from the lower surface of the tray, the wells capable of being filled through openings in the upper surface of the tray. The wells can be limited in size to contain a relatively small amount of liquid, e.g., less than one mL, and the multi-well plates containing the same are designated as micro-well plates. Alternatively, the wells can be expanded in size to contain a relatively large amount of liquid, e.g., greater than one mL, and the multi-well plates containing the same are merely designated as multi-well plates.

As used herein, the term "kitting" means dispensing samples and reagents in appropriate micro-wells of a micro-well plate prior to commencing chemical reactions.

As used herein, the symbol "(s)" following the name of an item indicates that one or more of the subject items is intended, depending upon the context. As used herein, the expression "and/or" is used to indicate that either the word "and" or the word "or" can be used to connect words, phrases, or clauses.

Throughout the specification, so far as possible, like parts or components will have the same reference numerals; like parts or components may have different reference numerals when required for the sake of clarity.

The apparatus and method described herein provides a subsystem for separating a solid magnetic substrate from the liquid contents of a reaction vessel in an immunoassay analyzer, i.e., a magnetic particle processor, to obtain direct access to a XYZ aspirating/dispensing device. Micro-well plates can be automatically inserted into and removed from the magnetic particle processor associated with the aforementioned subsystem. In addition, supplies for use in the magnetic particle processor can be automatically loaded onto and unloaded from certain mechanical components of the magnetic particle processor of the aforementioned subsystem.

The required control synchronization for the system described herein can be performed via a RS-232 interface on the aforementioned subsystem, and a USB interface on the aforementioned XYZ aspirating/dispensing device. These interfaces are illustrated schematically in FIG. 1. The components illustrated in FIG. 1 include a software module for absorbance readers, software for luminescence readers, software for magnetic particle processing, software for motor controllers, and software for dispensing devices. The foregoing programs are connected to the system software. The components also include appropriate connectors for interconnecting the aforementioned software.

Other components illustrated in FIG. 1 that are connected to the software module include an 8-axis motion controller, which is used to control the micro-well plate rotator, the apparatus for dispersing microparticles, the magnetic particle processing tray, and the radio frequency reader/writer, which can move in two directions in one plane. A temperature controller is connected to the plate rotator. The components also include appropriate electrical connectors for connecting to the aforementioned software module. It should be noted that the system does not require both at least one radio frequency identification antenna section board and at least one radio frequency identification reader/writer. One or the other or both of the foregoing radio frequency identification components can be used.

Still other components illustrated in FIG. 1 that are connected to the software module include at least one radio frequency identification antenna section board, at least one radio frequency identification reader/writer, at least one magnetic particle processor, at least one luminescence reader, at least one absorbance reader, at least one dispensing device platform. A temperature controller is connected to the at least one magnetic particle processor. The components also include appropriate electrical connectors for connecting to the aforementioned software module.

The components illustrated in FIG. 1 are commercially available and are capable of being connected in a proper manner by one having ordinary skill in the art.

A laboratory automation system that can use the computer interface illustrated in FIG. 1 and the loading system described herein is described in more detail in U.S. patent application Ser. No. 12/257,495, which has been filed as a non-provisional United States Patent Application on Oct. 24, 2008, and which claims priority from U.S. Provisional Application Ser. No. 60/985,373, filed Nov. 5, 2007, entitled AUTOMATED ANALYZER FOR CLINICAL LABORATORY, and furthermore, is incorporated herein by reference.

The system can read radio frequency identification tags attached to a micro-well plate. The magnetic particle processor can also be used as an incubator/mixer for immunoassays that do not utilize magnetic microparticles.

Referring now to FIGS. 2, 3, 4, 5, 6, and 9, a magnetic particle processor 10 has a left side panel 12 (partially shown), a top panel or cover 14 (partially shown), a bottom panel (not shown), a rear panel (not shown), a right side panel 18 (partially shown), and a front panel 16. The front panel 16 of the magnetic particle processor 10 comprises a rotatable upper portion 20, which has a closed position and an open position and a fixed lower portion 22. A typical size for the magnetic particle processor 10 is about 1 foot by 1 foot by 1 foot. In FIGS. 2, 3, 4, 6, and 9, the rotatable upper portion 20 is shown in the open position. The rotatable upper portion 20 is attached to the top panel or cover 14 by a first hinge 24 and a second hinge 26. The rotatable upper portion 20 also has a handle 28 to enable the user to manually open and close the rotatable upper portion 20. In typical operation, the rotatable upper portion 20 is opened and closed automatically. When the rotatable upper portion 20 is in the closed position, an edge 30 of the rotatable upper portion 20 abuts an edge 32 of the fixed lower portion 22. The rotatable upper portion 20 has an aperture 34 formed at the center of the edge 34 of the rotatable upper portion 20. The shape of the aperture 34 can be varied, but is must be of sufficient size to enable a supporting rail 36 to pass through it. The supporting rail 36 supports a supporting tray 38, which is capable of supporting at least one micro-well plate 40, and preferably two micro-well plates 40. The supporting rail 36 is fixed at the distal end thereof and is free at the proximal end thereof. The supporting rail 36 is sufficiently rigid and sufficiently strong to support both the supporting tray 38 and the equipment, e.g., motor, gears, screw, etc., that are required to move the supporting tray 38 into and out of the magnetic particle processor 10.

The supporting rail 36 allows the micro-well plate(s) 40 to be manipulated at some distance apart from the interior of the magnetic particle processor 10. The supporting rail 36 must be of a sufficient length to enable the supporting tray 38 to be extended a sufficient distance to be clear of the front panel 16. A sufficient distance is typically at least about one inch.

Figure 6:
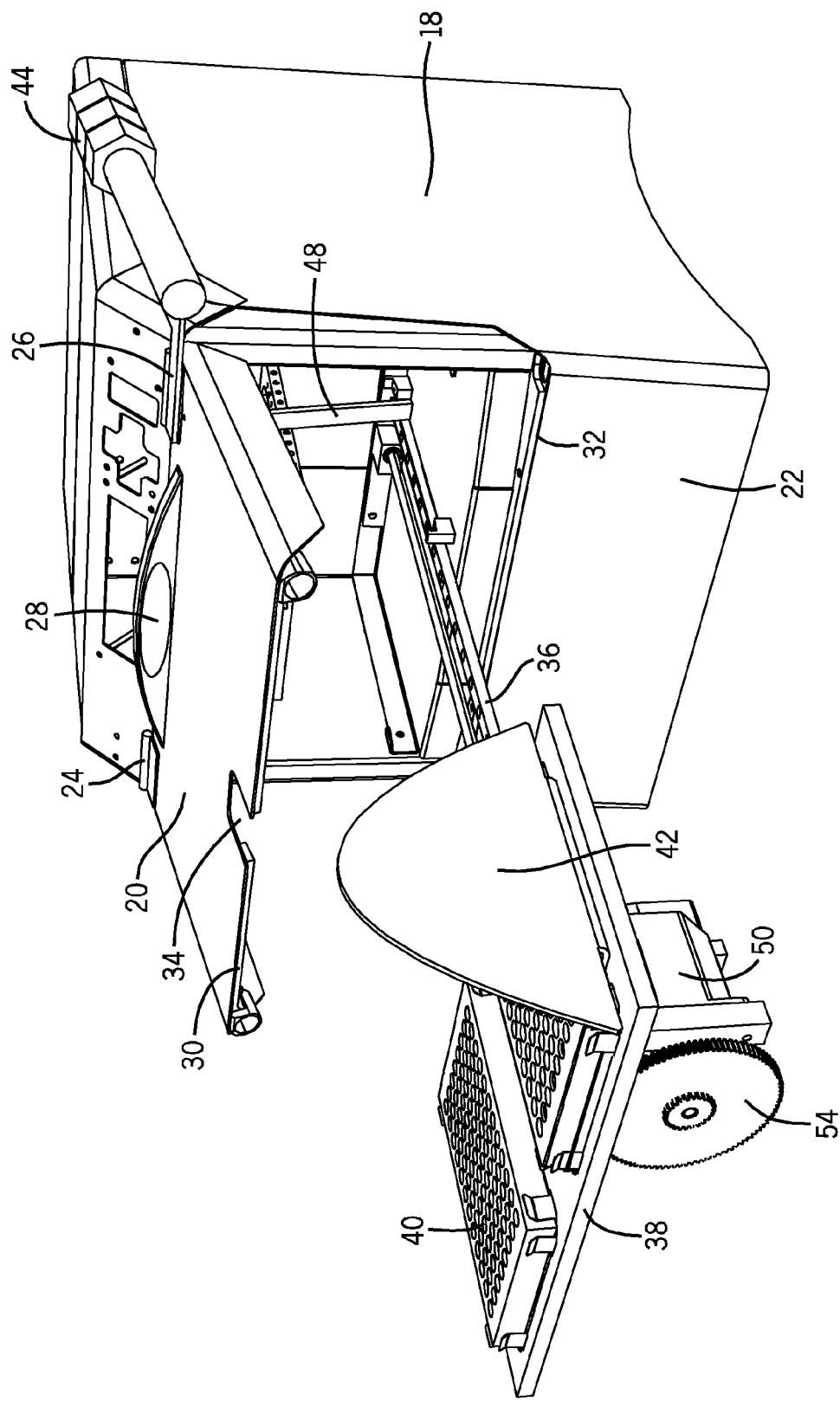
FIG. 6 is a perspective view illustrating the opposite side of the magnetic particle processor as shown in FIG. 2. In this figure, a tray for supporting a tip comb rack or micro-well plate is shown outside the magnetic particle processor.
Figure 9:
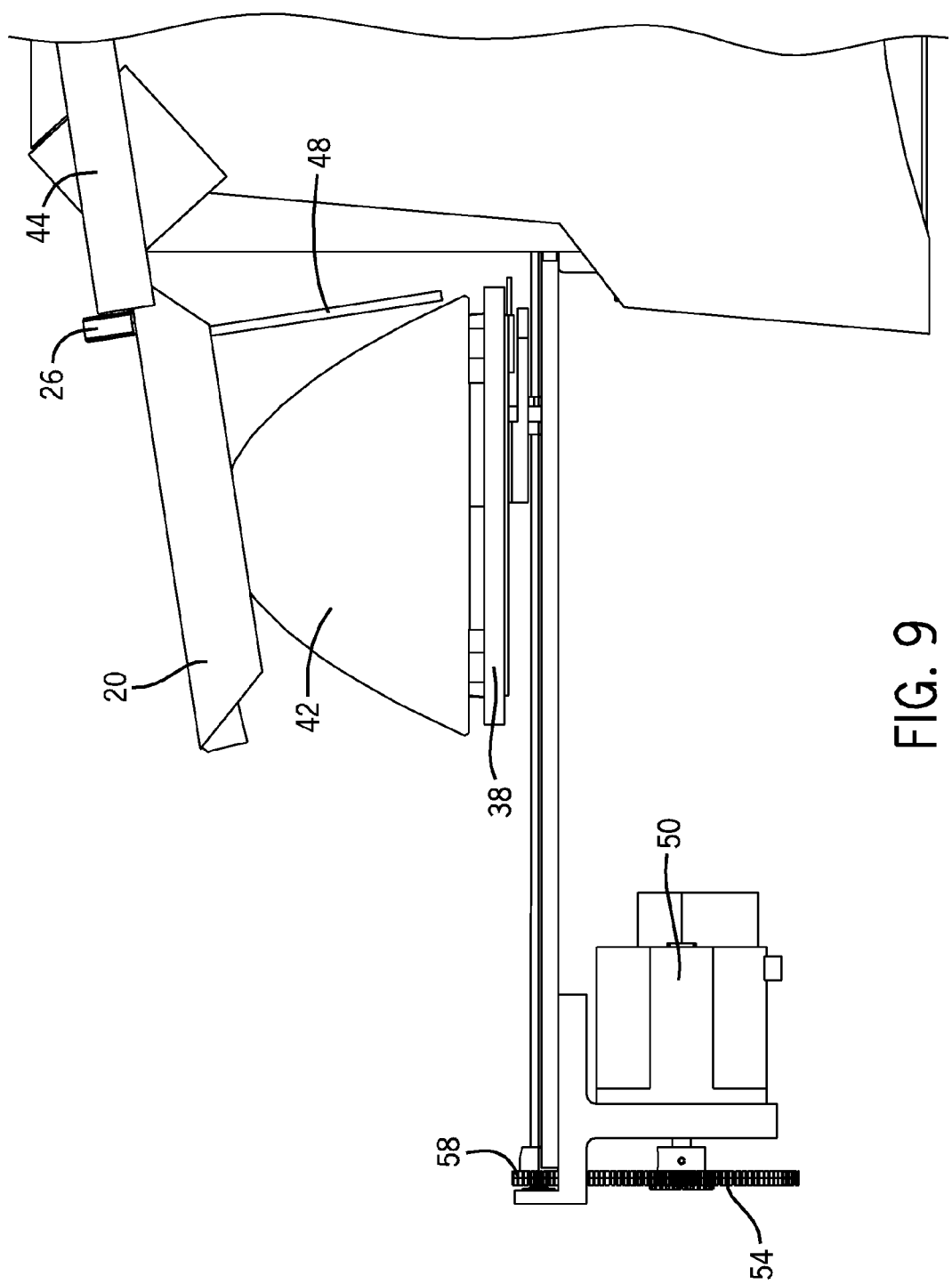
FIG. 9 is a side view in elevation illustrating the mechanism for opening the rotatable upper portion of the front panel of the magnetic particle processor. In this figure, a cam and a cam follower for opening and closing the magnetic particle processor is shown.

A system employing a cam and a cam follower system can be used to rotate the rotatable upper portion 20. Referring specifically now to FIGS. 6 and 9, a cam 42 is attached to the right side of the supporting tray 38. The cam 42 has a substantially parabolic shape. However, other shapes can be used in place of a parabolic shape. A counterweight 44 is attached to the rotatable upper portion 20 adjacent to the second hinge 26 induces the rotatable upper portion 20 to remain in the open position once the counterweight 44 has passed an angle measuring approximately 45° from the vertical. A cam follower 48 is positioned inside of the magnetic particle processor 10. The cam follower 48 has a shape corresponding to that of an elongated plate that traverses approximately one-half of the cam 42. The cam follower 48 remains in contact with the surface of the cam 42 until the rotatable upper portion 20 is approximately parallel to 28 is approximately parallel to the surface of the supporting tray 38, the rear edge of the supporting tray is approximately one inch away from the fixed lower portion 20. At that point the cam follower 48 is no longer in contact with the cam 42.

As stated previously, the cam 42 is attached to the right side of the supporting tray 38. The supporting tray 38 is capable of being driven along the supporting rail 36. The cam 42, which is attached to the supporting tray 38, moves away from the magnetic particle processor 10 when the supporting tray 38 moves away from the magnetic particle processor 10 and moves toward the magnetic particle processor 10 when the supporting tray 38 toward the magnetic particle processor 10. Movement of the cam 42 and contact of the cam 42 against the cam follower 48 actuates the cam follower 48.

Referring specifically now to FIGS. 5, 6, 8, and 9, a stepper motor 50, an encoder (not shown), a drive gear 54, a threaded lead screw 56, and a threaded nut (not shown) can be used to control the motion of the supporting rail 36 of the supporting tray 38 for the micro-well plate(s) 40. The encoder is used to verify (usually by observation of rotation) the movement of the motor. Encoders provide "counts" that can be used to verify and correct stepper motor movements. Encoders verify rotational movement and can be used to correct positional errors.

The stepper motor 50 rotates the drive gear 54. The drive gear 54 drives a driven gear 58. The threaded nut is thereby caused to move along the lead screw 56, which, in turn, causes the supporting rail 36 to move toward or away from the magnetic particle processor 10, depending upon which direction the drive gear 54 is rotating.

The rotatable upper portion 20 is of slightly lower weight than the counterweight 44. Accordingly, when the cam follower 48 breaks contact with the cam follower 48 as the supporting tray 38 is moved outwardly from the interior of the magnetic particle processor 10, the rotatable upper portion 20 swings outwardly from the magnetic particle processor 10 and remains open for the reason that the weight of the counterweight 44 exceeds that of the rotatable upper portion 20. The counterweight 44 is preferably on the same side of the magnetic particle processor 10 as are the cam 42 and the cam follower 48. The counterweight 44 is preferably attached to the rotatable upper portion 20 on the side of the second hinge 26 opposite from that of the top panel 14 and beyond the right side panel 18 of the magnetic particle processor 10 so that the rotatable upper portion 20 can be rotated to the fully open position.

When it is desired to close the rotatable upper portion 20, the cam 42 strikes the cam follower 48 and pushes against the cam follower 48, the movement of the cam follower 48 forces the counterweight 44 to return to a vertical position, whereby the rotatable upper portion 20 can be rotated to the fully closed position. The shape of the counterweight is not critical.

Figure 7:
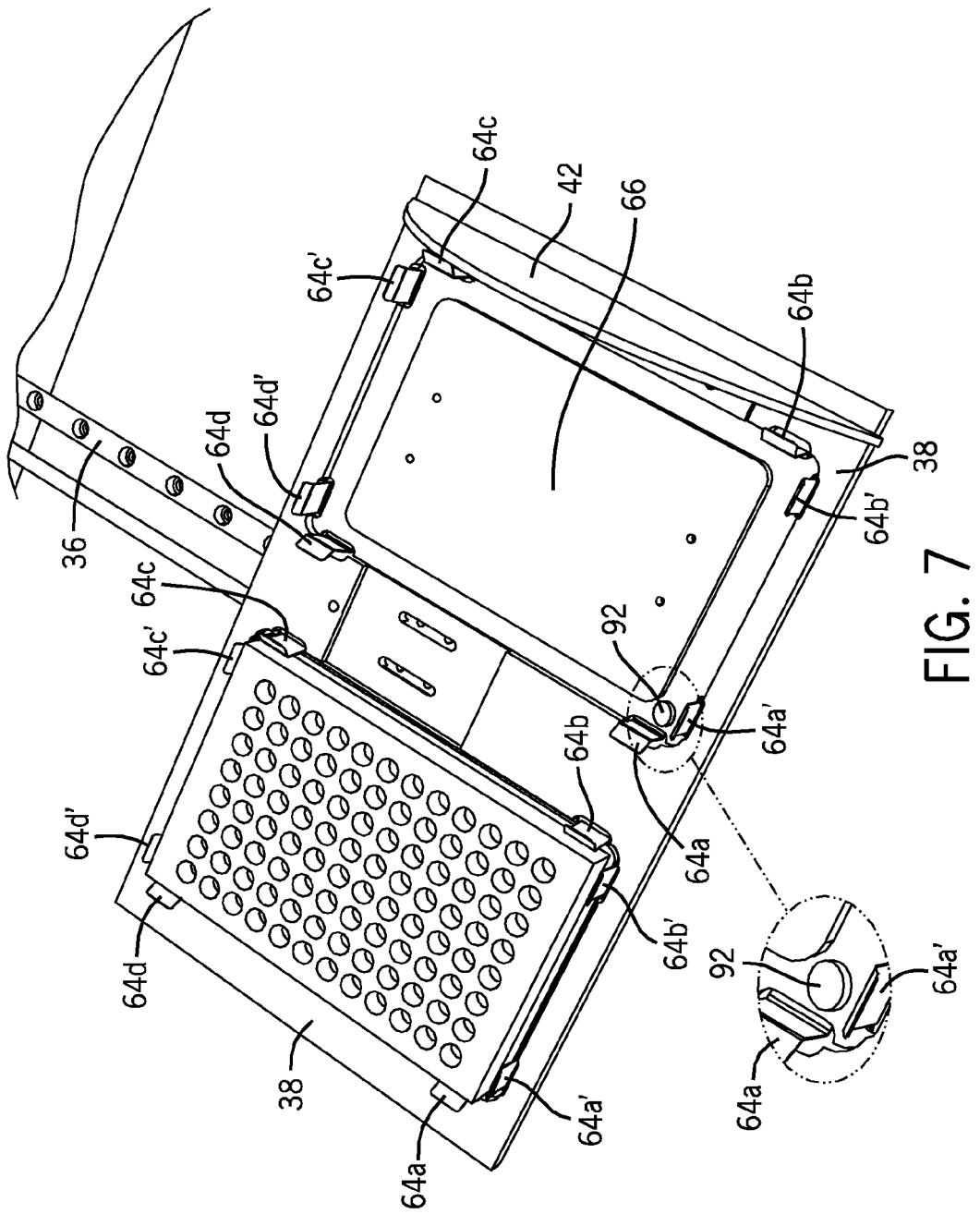
FIG. 7 is a perspective view, greatly enlarged, of the top surface of a supporting tray.
Figure 10A:
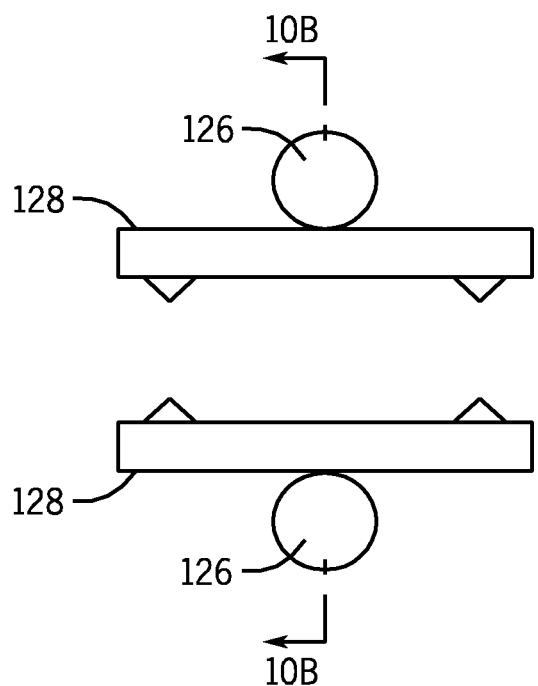
FIG. 10A is a schematic diagram illustrating the top view of gripping devices attached to an aspirating/dispensing device, the gripping devices gripping a micro-well plate.
Figure 10B:
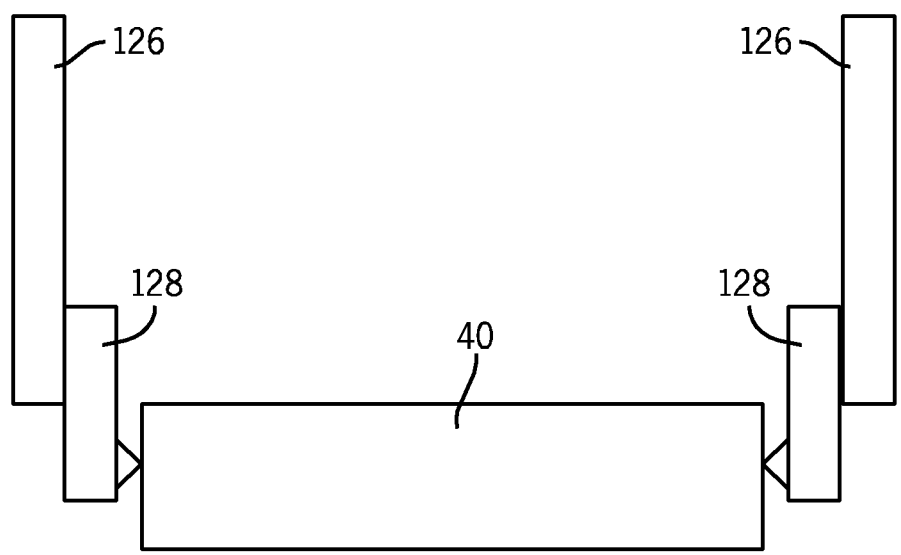
FIG. 10B is a schematic diagram illustrating a cross-sectional view of FIG. 9A taken along line 15B-15B.

Referring specifically now to FIG. 7, the supporting tray 38 for the micro-well plate(s) 40 utilizes resilient clips 64a, 64a', 64b, 64b', 64c, 64c', and 64d, 64d' to temporarily secure a micro-well plate 40 to the supporting tray 38. The resilient clips 64a, 64a', 64b, 64b', 64c, 64c', and 64d, 64d' are preferably beveled in order to enable a micro-well plate 40 to be properly placed on the supporting tray 38 even if the micro-well plate 40 is not exactly aligned with the resilient clips 64a, 64a', 64b, 64b', 64c, 64c', and 64d, 64d'. The resiliency of the resilient clips 64a, 64a', 64b, 64b', 64c, 64c', and 64d, 64d' enables the micro-well plate to be placed by means of a XYZ aspirating/dispensing device that moves vertically. The XYZ aspirating/dispensing device first selects a micro-well plate from a storage area (not shown) for micro-well plates 40, grips the micro-well plate 40 as shown in FIGS. 10A and 10B, transfers the micro-well plate 40 to a position above the supporting tray 38 of the magnetic particle processor 10 and in register with the upraised portion 66 of the supporting tray 38, and then lowers the micro-well plate 40 onto the upraised portion 66 of the supporting tray 38. The micro-well plate 40 is secured by the resilient clips 64a, 64a', 64b, 64b', 64c, 64c' and 64d, 64d' located at the corners of the upraised portion 66 of the supporting tray 38. Details of the vertical placement of a micro-well plate 40 onto the supporting tray 38 are described later in reference to the XYZ aspirating/dispensing device.

The supporting tray 38 also has at least one upraised portion 66, of such a depth and of such areal dimensions so as to be substantially equal in the size to the micro-well plate 40, so that heat transfer from the at least one upraised portion 66 to the bottom of the micro-well plate 40 is maximized. The at least one upraised portion 66 supporting tray 38 is formed of a thermally conductive material, such as, for example, a thermally conductive metal or alloy, e.g., aluminum or an aluminum alloy. The base of each micro-well of the micro-well plate 40 should be in contact with the upper surface of the upraised portion 66. The depth of and the material of the upraised portion 66 of the supporting tray 38 facilitate the transfer of heat into the micro-wells of the micro-well plate 40. A typical depth of the upraised portion 66 of the supporting tray 38 is about one quarter inch. A typical depth of a micro-well plate 40 is about one half inch. It is within the scope of this invention to utilize a supporting tray 38 characterized by ball-cut indentations to enable the supporting tray 38 to conform to a micro-well plate having ninety-six (96) round-bottom micro-wells. Such a ball-cut supporting tray 38 would provide the maximum surface contact with a micro-well plate 40 and most efficient heat transfer between the supporting tray 38 and the micro-well plate 40.

Figure 8:
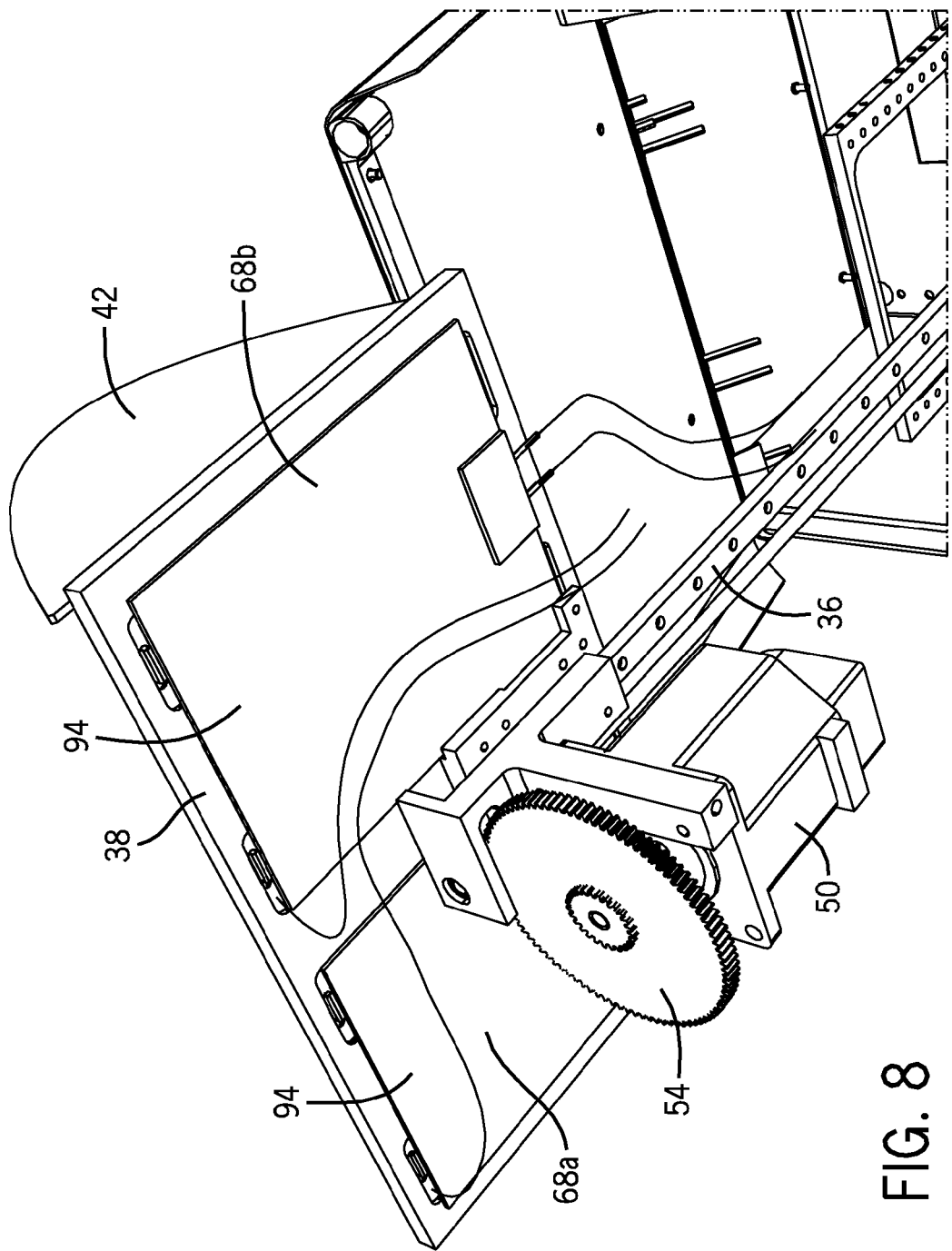
FIG. 8 is a perspective view, greatly enlarged, of the bottom surface of a supporting tray. In this figure, the motor and the gear for moving the supporting tray are also shown.

Referring specifically now to FIG. 8, heater pads 68a, 68b positioned below the supporting tray 38 and in contact therewith are larger in areal dimensions than is the upraised portion 66 of the supporting tray 38 and micro-well plate 40. It is preferred that the compartment where the supporting tray 38 for the micro-well plate(s) 40 resides during magnetic particle processing be insulated. The interior walls of the magnetic particle processor 10 and the interior surface of the rotatable upper portion 20 and the interior surface of the fixed lower portion 22 can be insulated, typically with insulation rated at least R-18. A type of insulation suitable for use herein is aluminized air pocket insulation, approximately one-quarter inch thick, and commercially available from Home Depot.

The two heater pads 68a, 68b (100 watts, 4 inches by 5 inches) are adhered to the underside of the supporting tray 38, typically by a pressure-sensitive adhesive. As described previously, the upper surface of the supporting tray 38 for the micro-well plate 40, below the area for positioning the micro-well plates 40 (the tray holds two micro-well plates) has been raised, i.e., the upraised portion 66, and shaped to match the bottom surface of the micro-well plates 40 and to contact the bottom surface of the micro-well plates 40 to improve heat transfer to the micro-well plates 40 by means of conduction.

A proportional, integral, derivative (PID) temperature controller and a resistive temperature detector (RTD), adhered to the supporting tray 38, typically by means of an epoxy adhesive, can be used to control the temperature of incubation during magnetic particle processing. The proportional, integral, derivative (PID) temperature controller dampens the system response, corrects for droop, and prevents overshoot and undershoot, whereby overshoot is significantly reduced. The proportional, integral, derivative (PID) temperature controller modifies the duty cycle of the heater current. The resistive temperature detector (RTD) is preferably a thermistor. A thermistor is a temperature-sensing device made of a semiconductor material that exhibits a large change in resistance for a small change in temperature. Thermistors usually have negative temperature coefficients, although they are also available with positive temperature coefficients. Other resistive temperature detectors, such as for example, a wire RTD, can be used in place of a thermistor. Proportional, integral, derivative (PID) temperature controllers and a resistive temperature detectors (RTD) are commercially available from Watlow Electric Manufacturing Company, St. Louis, Mo. Optionally, an independent temperature-monitoring device can be added for magnetic particle processors expected to be used in blood banks.

There are several alternatives for the rotatable upper portion 20. For example, the front panel 16 could be separately actuated, and have the hinges 24 and 26 repositioned at the lower edge 16*a* of the front panel 16. This modification may be preferred, because the position of the hinges 24 and 26 at the upper edge 16*b* of the front panel 16 forces the supporting tray 38 to be transported further away from the magnetic particle processor (so that loading and unloading of the supporting tray 38 can be performed from a position above the supporting tray 38). However, the embodiment illustrated minimizes the number of actuators required.

Figure 11A:
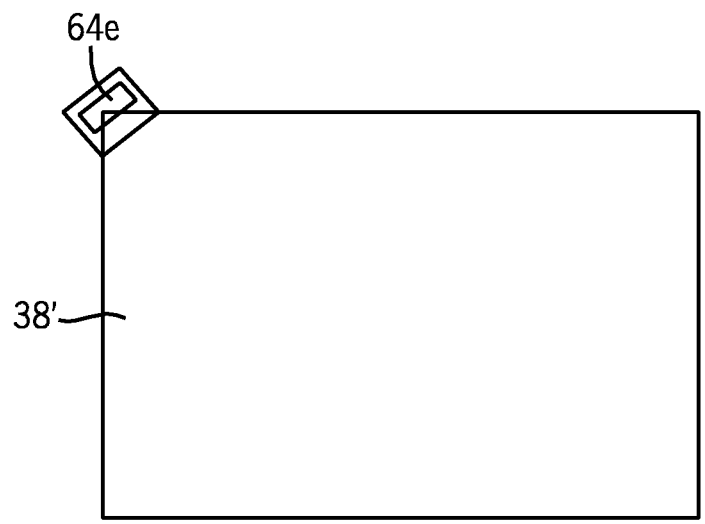
FIGS. 11A, 11B, and 11C are schematic views illustrating an alternative mechanism for placing a micro-well plate in position for a magnetic particle processing operation.
Figure 11B:
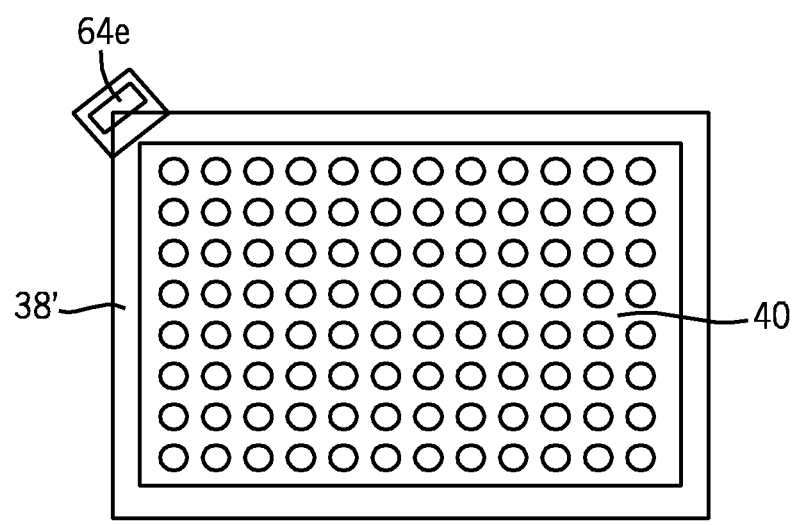
Figure 11C:
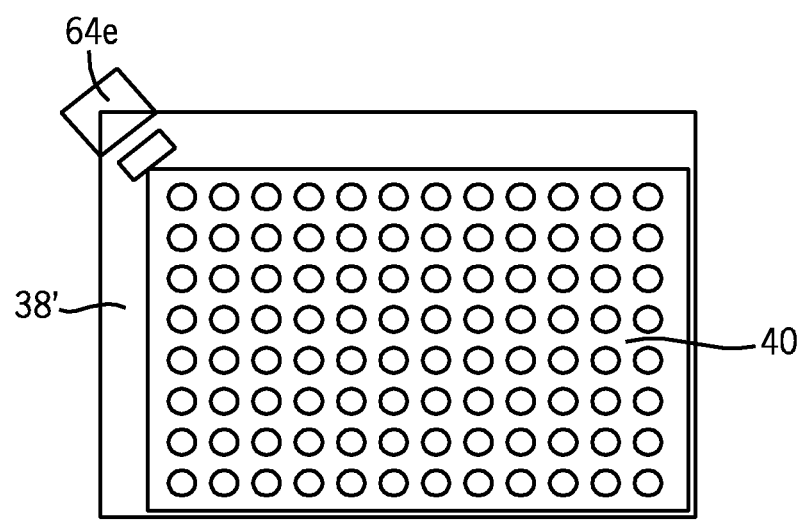

There are also several alternatives for providing proper registration for the micro-well plate in the magnetic particle processor. For example, registration of the micro-well plate 40 can be performed by a squeezing mechanism that forces the micro-well plate 40 into contact with the distal end of a supporting tray 38' when the supporting tray 38' has been transported into the magnetic particle processor 10. In the alternative utilizing the squeezing mechanism, the micro-well plate 40 is placed loosely onto a supporting tray 38', which has no resilient clips thereon, as shown in FIGS. 11A and 11B. Instead, the supporting tray 38' has boundary walls (not shown) rising vertically at the back end 38*a'* and at the sides 38*b'* and 38*c'* of the supporting tray 38'. After the micro-well plate 40 is placed on the supporting tray 38', the squeezing mechanism 64*e* is actuated, as shown in FIG. 11C. The squeezing mechanism 64*e* pushes the micro-well plate 40 a small distance until the micro-well plate 40 contacts the boundary walls 38*a'* and 38*b'* of the supporting tray 38', at which point the micro-well plate 40 is in register with the operating components of the magnetic particle processor 10.

Figure 12:
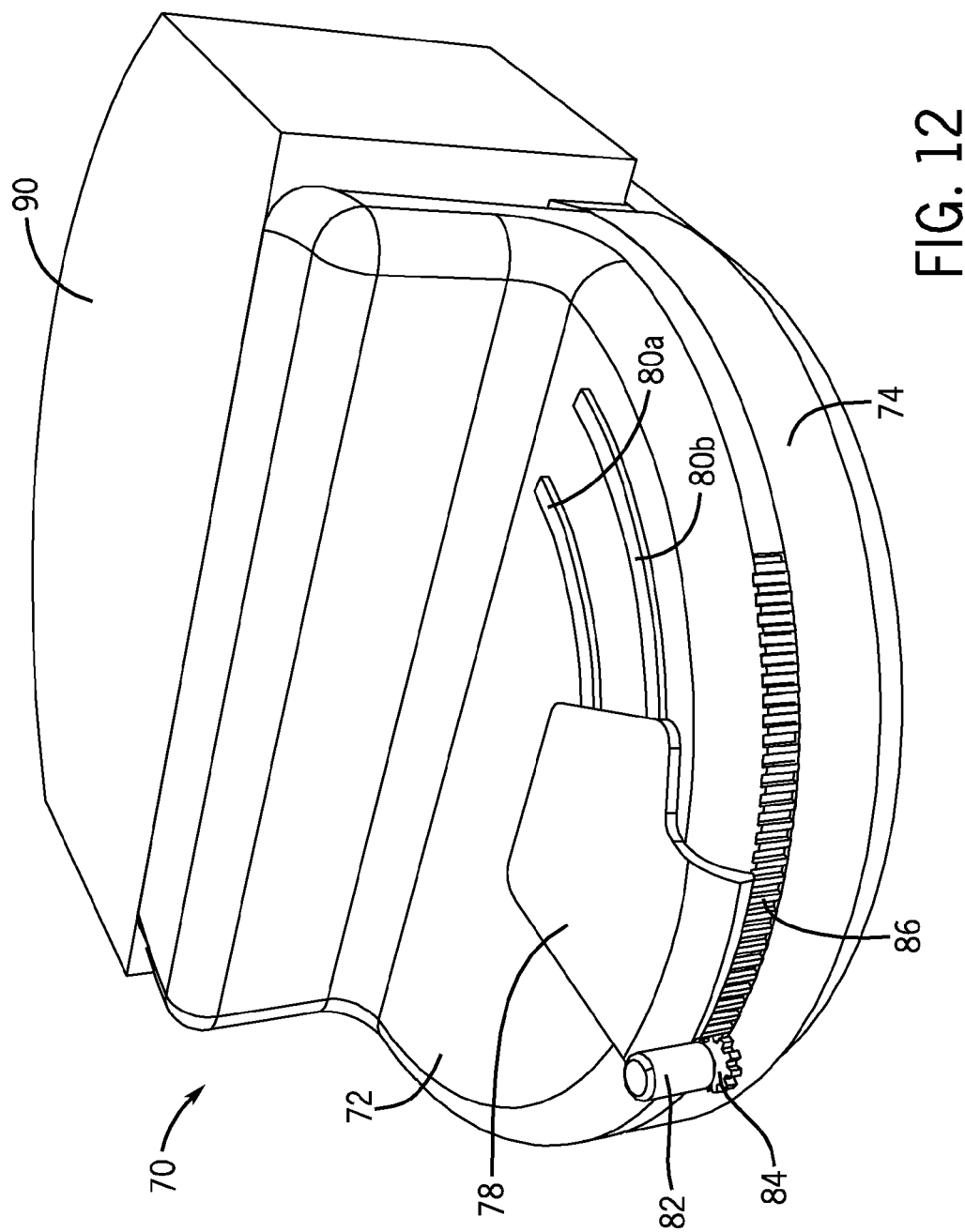
FIG. 12 is a perspective view of a magnetic particle processor based on a version of a commercially available magnetic particle processor known as KingFisher™ 96 magnetic particle processor. In this figure, a movable cover is blocking the opening to the interior of the magnetic particle processor.
Figure 13:
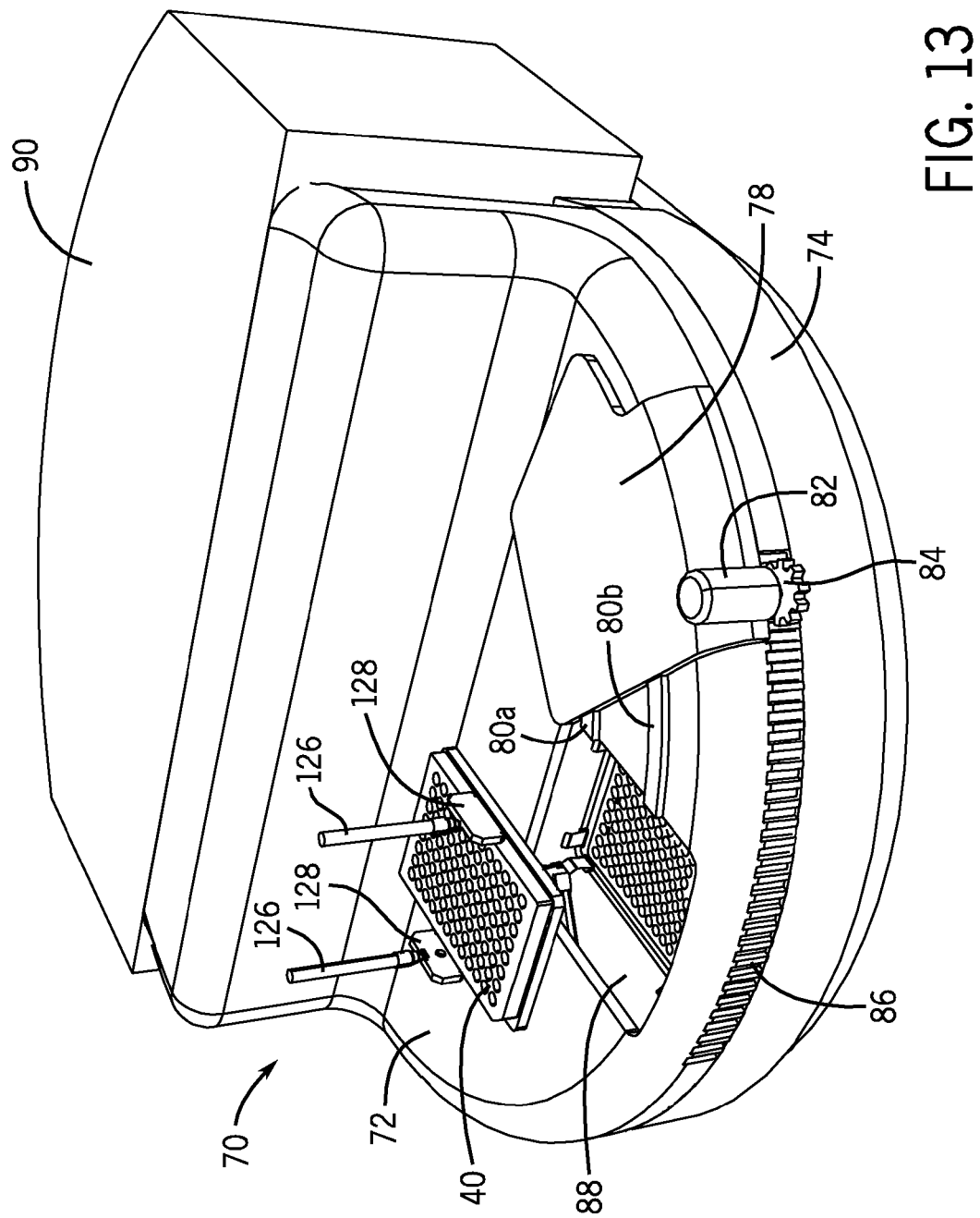
FIG. 13 is a perspective view of a magnetic particle processor shown in FIG. 12. In this figure, the movable cover is moved to expose the opening to the interior of the magnetic particle processor.
Figure 14:
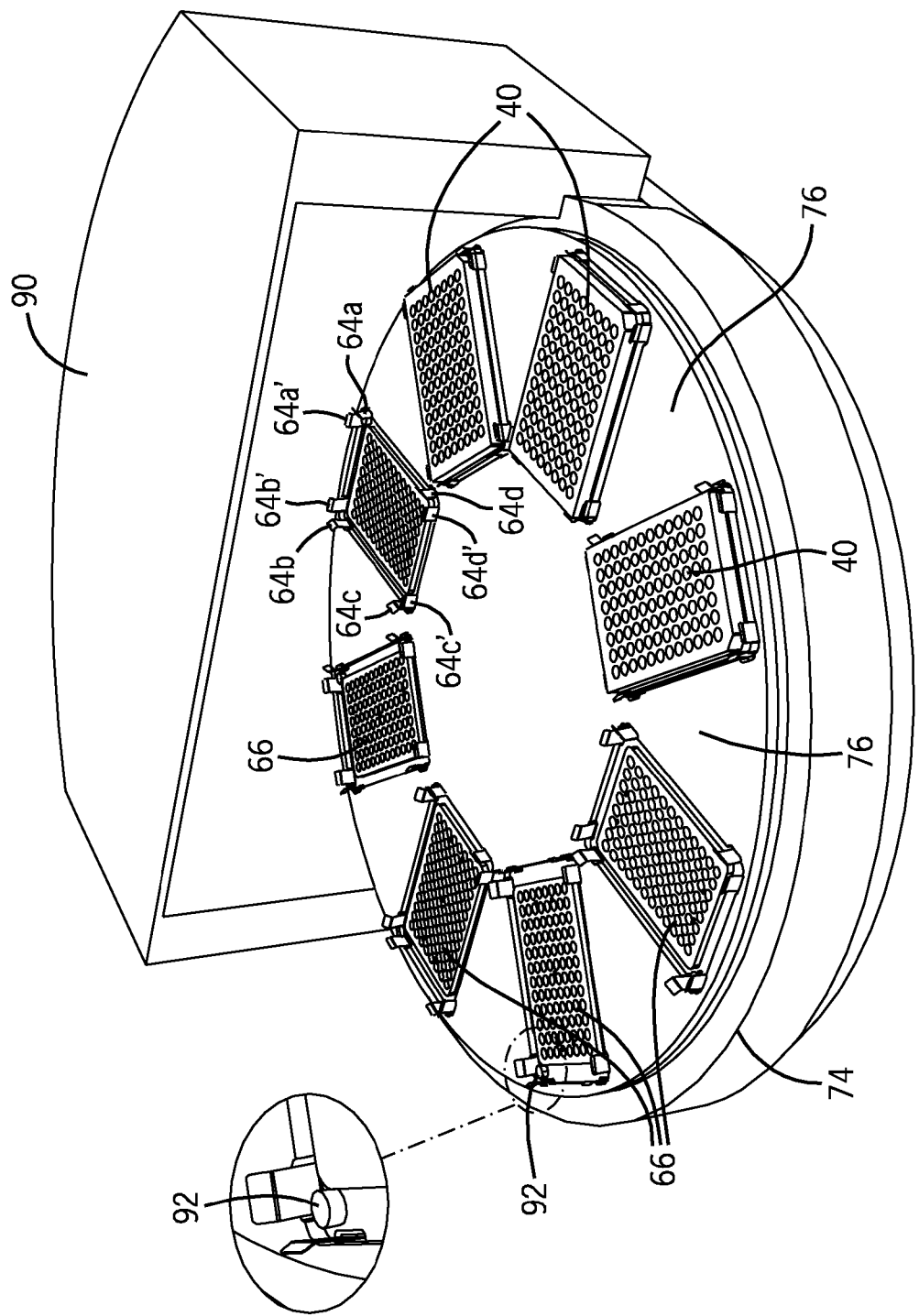
FIG. 14 is a perspective view of a turntable that is located in the interior of the magnetic particle processor shown in FIGS. 12 and 13.
Figure 15:
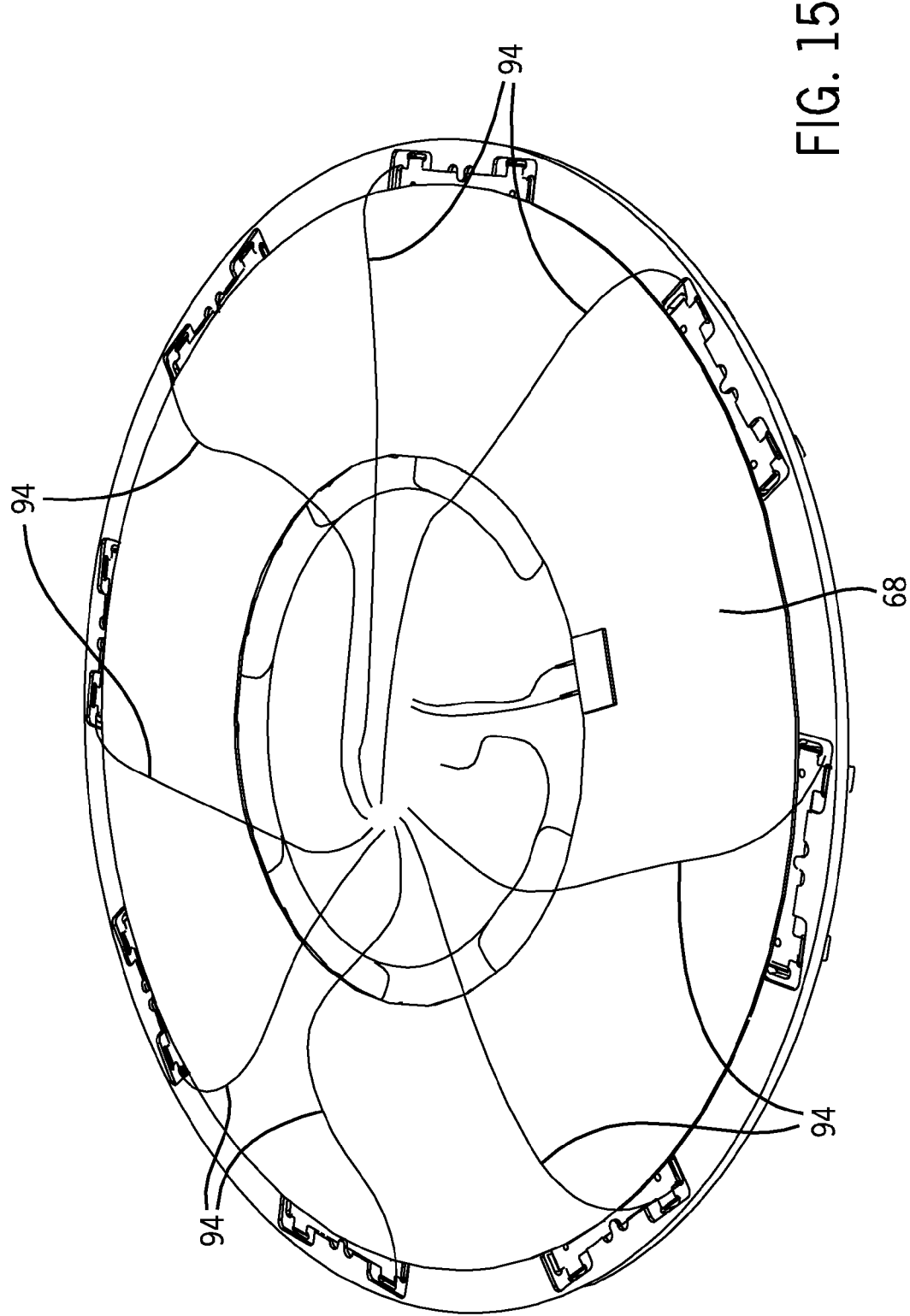
FIG. 15 is a perspective view of radio frequency identification cables for the magnetic particle processor shown in FIGS. 12, 13, and 14.

In another embodiment of the magnetic particle processor, a modified version of the KingFisher™ 96, commercially available from Thermo Fisher Scientific, Inc., Waltham, Mass., the micro-well plates 40 are inserted vertically, as shown in FIGS. 12, 13, 14, and 15. Referring now to FIGS. 12, 13, 14, and 15, a magnetic particle processor 70 can contain up to eight micro-well plates 40. As shown in FIGS. 12, 13, and 14, the magnetic particle processor 70 comprises an enclosure comprising an upper portion 72 and a lower portion 74. The upper portion 72 functions as a cover for the micro-well plates 40. As can be seen in FIG. 14, the magnetic particle processor 70 comprises a circular turntable 76 capable of positioning and supporting eight micro-well plates 40. Access to the positions for placing the micro-well plates 40 can be gained by moving a movable plate 78 attached to the upper portion 72 of the magnetic particle processor 70. The movable plate 78 is capable of moving along a pair of tracks 80*a*, 80*b* formed on the surface of the upper portion 72 of the magnetic particle processor 70. An edge 78*a* of the movable plate 78 adjacent to the circumferential edge 72*a* of the upper portion 72 of the magnetic particle processor 70 overhangs the sidewall 72*b* of the upper portion 72 of the magnetic particle processor 70. Attached to this overhanging edge 78*a* of the movable plate 78 is a motor 82, typically a stepper motor. The motor 82 has a shaft (not shown) upon which is mounted a small gear 84. The teeth of the small gear 84 mesh with the teeth of a stationary gear 86 formed on the magnetic particle processor 70 at the interface between the upper portion 72 and the lower portion 74 of the magnetic particle processor 70. Upon a signal provided by pulse generator, such as, for example, a square wave pulse generator associated with a stepper motor driver, the motor 82 is actuated, whereby the shaft rotates and the small gear 84 travels over the teeth of the stationary gear 86, with the result that the movable plate 78 travels along the tracks 80*a*, 80*b* until an opening 88 is exposed a sufficient amount to enable a micro-well plate 40 to be inserted through the opening 88 and onto the circular turntable 76. The turntable 76 in the magnetic particle processor 70 has a plurality of upraised portions 66, analogous to the at least one upraised portion 66 on the supporting tray 38 in the embodiment shown in FIG. 7. The micro-well plates 40 are placed upon these upraised portions 66. Analogous to the supporting tray 38, each position for a micro-well plate 40 in the turntable 76 comprises a plurality of resilient clips 64*a*, 64*a'*, 64*b*, 64*b'*, 64*c*, 64*c'*, and 64*d*, 64*d'* to securely retain the micro-well plate 40 during magnetic particle processing. Also, each position for a micro-well plate in the turntable 76 comprises a heater pad 68*c* analogous to the heater pads shown in FIG. 8. The micro-well plate is placed onto the upraised portion 66 by means of a XYZ aspirating/dispensing device of a type mentioned previously and to be described later. After the movable plate 78 is moved a sufficient distance to enable a micro-well plate 40 to be inserted through the opening 88, the XYZ aspirating/dispensing device first selects a micro-well plate from a storage area (not shown) for micro-well plates 40, grips the micro-well plate 40 as shown in FIG. 13, transfers the micro-well plate 40 to a position above the magnetic particle processor 70 and in register with the upraised portion 66 of the turntable 76, and then lowers the micro-well plate 40 onto the upraised portion 66 of the turntable 76. The micro-well plate 40 is secured by the resilient clips 64*a*, 64*a'*, 64*b*, 64*b'*, 64*c*, 64*c'*, and 64*d*, 64*d'* located at the corners of the upraised portion 66 of the turntable 76. The magnetic rods, the tip combs, and other components for carrying out magnetic particle processing operations are located in the rear section 90 of the magnetic particle processor 70.

In both embodiments, i.e., the embodiment derived from the KingFisher™ magnetic particle processor, shown in FIGS. 2, 3, 4, 5, 6, 7, 8, and 9, and the embodiment derived from the KingFisher™ 96 magnetic particle processor, shown in FIGS. 12, 13, 14, and 15, a high frequency antenna 92 is located at one corner of each micro-well plate 40. This antenna 92 is capable of being selectively connected to a radio frequency identification reader (not shown) by means of a radio frequency cable 94 and an antenna board. The radio frequency cable is a low loss, flexible cable, such as, for example, a RG316 cable, or equivalent. When selected by the antenna board (see FIG. 1), the remote antenna 92 will be connected to the radio frequency identification reader. This radio frequency identification reader provides the capability of reading a radio frequency identification tag (not shown) that has been applied to each micro-well plate 40. This reading provides verification of geometric orientation, for position A1 of the micro-well plate, and chain of custody tracking of a micro-well plate 40. In a micro-well plate 40, rows are designated by letters, i.e., A, B, C, etc. and columns are designated by numerals, i.e., 1, 2, 3, etc. Position A1 refers to row A, column 1.

The immunoassay processor(s) described herein provides the following functions: incubation of reaction mixtures, mixing of reaction mixtures, separation of components from reaction mixtures, washing of reaction product(s), and release of label to enable reading of the results of immunoassays. An immunoassay processor 100 that can be modified for use herein is a KingFisher™ magnetic particle processor, commercially available from Thermo Fisher Scientific, Inc., Waltham, Mass., and described in U.S. application Ser. No. 11/923,828, filed Oct. 25, 2007, and entitled METHOD OF PERFORMING ULTRA-SENSITIVE IMMUNOASSAYS, incorporated herein by reference. Other magnetic particle processors that can be modified for use in certain embodiments described herein include KingFisher™ 96 magnetic particle processor, commercially available from Thermo Fisher Scientific, Inc., Waltham, Mass. This type of immunoassay processor is depicted in FIGS. 12, 13, 14, and 15, and designated by the reference numeral 70. In the embodiment wherein the label is a chemiluminescent label, the release of label is carried out in a manner similar to that used in the ARCHITECT® analyzer, as described in U.S. Pat. Nos. 5,795,784 and 5,856,194, both of which are incorporated herein by reference. The trigger solution is dispensed during the reading of a reaction product in a well.

As a result of these enhancements, separating a solid magnetic substrate from the liquid contents of a reaction vessel is combined with an incubation operation in a magnetic particle processor.

A synchronization controller is required in order to coordinate the movements of the XYZ aspirating/dispensing device, the magnetic particle processor, and the motor driving the supporting tray, which, in turn, moves the rotatable upper portion 20 of the magnetic particle processor; the synchronization controller can be a RS-232 interface on the magnetic particle processor, and a USB interface on the XYZ aspirating/dispensing device. As discussed earlier, micro-well plates 40 can be automatically loaded and unloaded by means of gripping devices on the pipettes of the XYZ aspirating/dispensing device.

Figure 16:
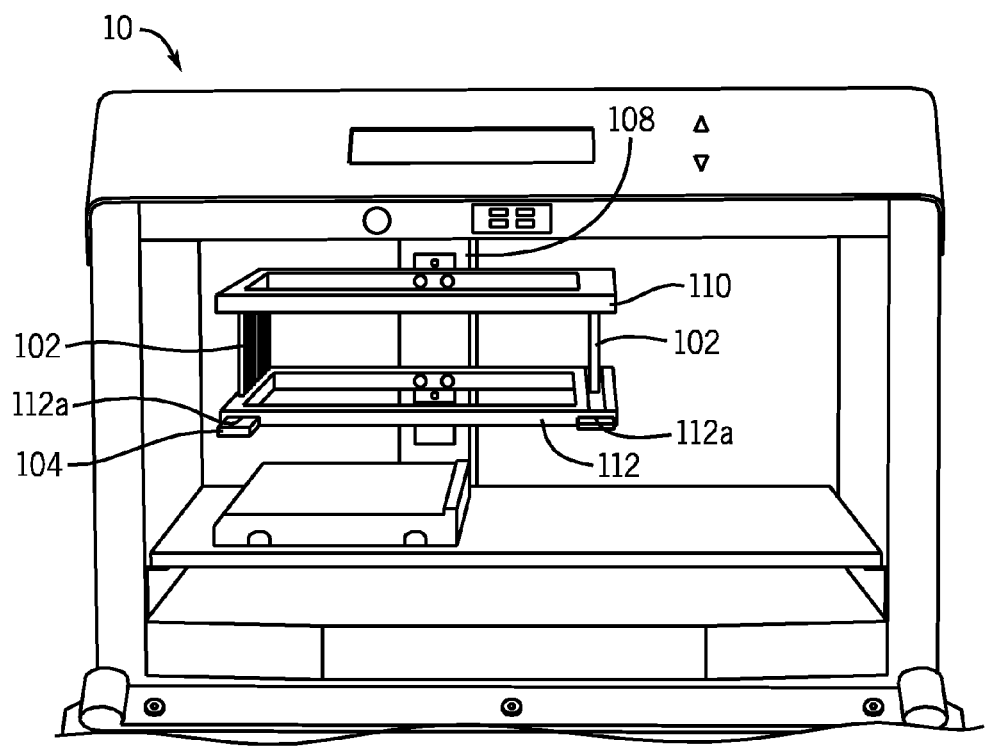
FIG. 16 is a front view in elevation of a commercially available magnetic particle processor.
Figure 17:
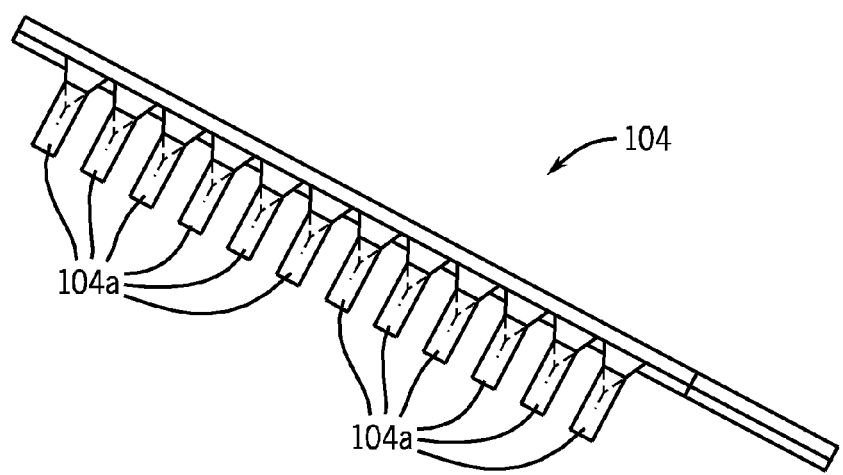
FIG. 17 is a front view in elevation of a tip comb suitable for use in the magnetic particle processor shown in FIG. 16.

Referring now to FIG. 16, the principle of the operation of the magnetic particle processor 100 is based on the use of (a) magnetic rods 102 that can be covered with the tips or sheaths of disposable tip combs 104 and (b) micro-well plates. New tip combs 104 are installed in the magnetic particle processor 10 prior to processing each micro-well plate 40. A tip comb 104 comprises a strip of non-magnetic material that joins a plurality of tips 104a, or sheaths, made of non-magnetic material, which tips, or sheaths, cover the magnetic rods 102. Commercially available tip combs 104 comprise twelve tips 104a, as shown in FIG. 17, for a magnetic particle processor that processes twelve samples simultaneously and 96 tips for a magnetic particle processor that processes 96 samples simultaneously.

The magnetic particle processor 100 is capable of carrying out magnetic particle processing steps without any aspirating and/or dispensing devices during magnetic particle processing. The magnetic particle processor 100 is designed for a maximum of two micro-well plates 40, each of which has 96 micro-wells. The micro-well plates 40 are compatible with the tip combs 104. The micro-well plates are maintained stationary and the only moving assembly is a processing head 108 with tip combs 104 and magnetic rods 102. The processing head 108 consists of two vertically moving platforms 110, 112. One platform 110 is needed for the magnetic rods 102 (2×12 rods) and the other platform 112 is needed for the plastic tip combs 104. The platforms are rectangular metal frames that can be moved in both a horizontal direction, to move from one micro-well to another, and in a vertical direction to enter or exit a micro-well and to agitate magnetic particles in a micro-well. The platforms 110 and 112 are shown in FIG. 16.

A single micro-well plate contains twelve columns and eight rows of micro-wells and processing of one sample typically uses up to eight micro-wells of a given row. In certain embodiments two micro-well plates can be employed, whereby more than eight micro-wells can be used to carry out an immunoassay. One tip comb 104 containing twelve tips is used for processing twelve samples at a time within one micro-well plate, each sample requiring a separate column.

The dimensions of the micro-wells are compatible with the dimensions of the tip comb 104 and the tips, or the sheaths, thereof, with the result that the tips can be used to mix or agitate the contents of the micro-well. A single sample processing for an immunoassay can be carried out in a single micro-well plate 40 containing ninety-six (96) micro-wells.

The operating principle employed by the magnetic particle processor is inverse magnetic particle processing technology, commonly referred to as MPP. Rather than moving liquids from one micro-well to another micro-well, the magnetic particles are moved from one micro-well to another micro-well, e.g., from a micro-well in a given column and row of a micro-well plate to a micro-well in the same column and in another row of the micro-well plate, at least one micro-well containing reagent(s) required for the immunoassay. This principle stands in contrast to the external magnet method, which is used in such automated analyzers as the ARCHITECT® analyzer, commercially available from Abbott Laboratories, Abbott Park, Ill. According to inverse magnetic particle processing technology, magnetic particles are transferred with the aid of the magnetic rods 102 covered with the disposable, specially designed plastic tip combs 104.

Figure 18:
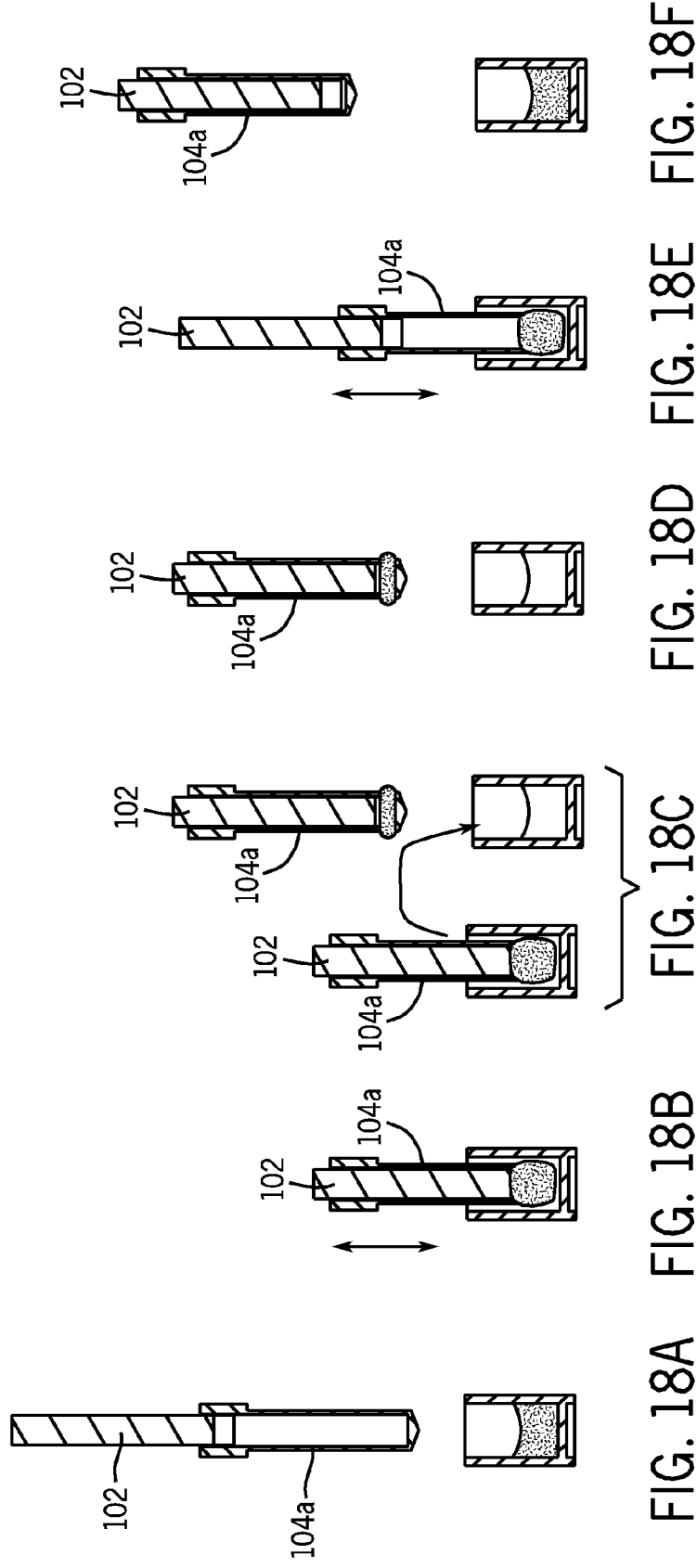
FIGS. 18A, 18B, 18C, 18D, 18E, and 18F are schematic diagrams illustrating a basic process that can utilize the principles of a KingFisher™ magnetic particle processor to process immunoassay reactions.

FIGS. 18A, 18B, 18C, 18D, 18E, and 18F illustrate schematically basic elements of the inverse magnetic particle processing. FIG. 18A shows a suspension of magnetic particles in a micro-well before collection. FIG. 18B shows the collection of magnetic particles. FIG. 18C shows the transfer of magnetic microparticles from one micro-well to another micro-well. FIG. 18D shows the magnetic particles on the surface of a tip of the tip comb. FIG. 18E shows the release of magnetic particles in the micro-well. FIG. 18F shows a suspension.

Working with magnetic particles can be divided into at least six separate process steps:

Collecting particles: In this step, magnetic particles are collected from the micro-well specified.

Binding particles: In this step, material is collected onto the magnetic particles from the reagent in a specific micro-well.

Mixing particles: In this step, the reagent and particles (if inserted), are mixed with the plastic tip in a specific micro-well.

Releasing particles: In this step, the collected material is released from the surfaces of the magnetic particles into a specific micro-well.

Washing particles: In this step, the magnetic particles are washed in a specific micro-well.

Incubation of reaction mixtures: In this step the temperature of the reaction mixture is elevated to a sufficient level to obtain a satisfactory specific binding reaction. This step can be carried out at the same time as are the five steps listed previously.

During the collection of the magnetic particles from the micro-wells of a micro-well plate, the magnetic rods 102 are fully enclosed by the tips, or the sheaths, of the tip comb 104. The magnetic rods 102 together with the tip comb 104 move slowly up and down in the micro-wells, and the magnetic particles are collected onto the walls of the tips, or the sheaths, of the tip comb 104. The magnetic rod 102 together with the tip comb 104, having collected the magnetic particles, can be lifted out of one column of micro-wells and transferred into the next column of micro-wells required by the process, etc. After collection of the magnetic particles, the magnetic rods 102 together with the tip comb 104 are lifted from the microwells, the magnetic rods 102 are lifted out of the tips, or the sheaths, and the tips, or the sheaths, of the tip comb 104 are lowered into the next micro-well containing a reagent. Magnetic particles are released by moving the tip comb 104 up and down several times at considerably high speed until all the particles have been mixed with the contents located in the succeeding row of micro-wells of the micro-well plate. This process can be carried out for twelve (12), twenty-four (24), or ninety-six (96) immunoassay reactions simultaneously.

Washing the magnetic particles is a frequent and an important phase of the magnetic particle processing activity. Washing is a combination of the release step and the collection step in a micro-well filled with a washing solution. To maximize washing efficiency in the micro-wells of a micro-well plate, the magnetic rods 102 together with the tip comb 104 are designed to have minimized liquid-carrying properties. To keep the suspension containing the magnetic particles evenly mixed in long-running reactions, the tip comb 104 can be moved up and down from time to time.

Inverse magnetic particle processing provides a micro-well plate format. Inverse magnetic particle processing eliminates the need for a process path of the type use in an ARCHITECT® analyzer, eliminates loaders for reaction vessels, eliminates mixers, and eliminates process path washing mechanisms, which typically operate in accordance with a fixed protocol. Inverse magnetic particle processing allows kitting and eliminates the need for time-dependent additions of critical reagents and other liquids.

It is desired to have the temperature of the liquid in a micro-well in a micro-well plate to be at temperature of 37° C. during the time required to kit the micro-well plate for an immunoassay. In summary, the temperature of the kitting area (not shown) will be set (via RS-232 interface) so that the final temperature of the first liquids dispensed into the micro-wells of the micro-well plate reaches a temperature of 37° C. in the time required to dispense the remaining liquids. In other words, the liquids wherein temperature is critical are dispensed first. During magnetic particle processing, the temperature of the liquids within the micro-well plates 40 should be maintained at a temperature of 37° C. Proper maintenance of the temperature during magnetic particle processing is ensure by the heater pads 68a, 68b, and the insulation of the of the magnetic particle processor 10. Similarly, the heater pads and the insulation in the magnetic particle processor 70 ensure proper maintenance of the temperature of the liquids within the micro-well plates 40 during magnetic particle processing.

During the magnetic particle processing operation, the rotatable upper portion 20 of the magnetic particle processor 10 and the top panel or cover 14 can be closed or can remain open. Closed lids and other closed panels protect the processing against environmental contamination and loss of heat.

Figure 2:
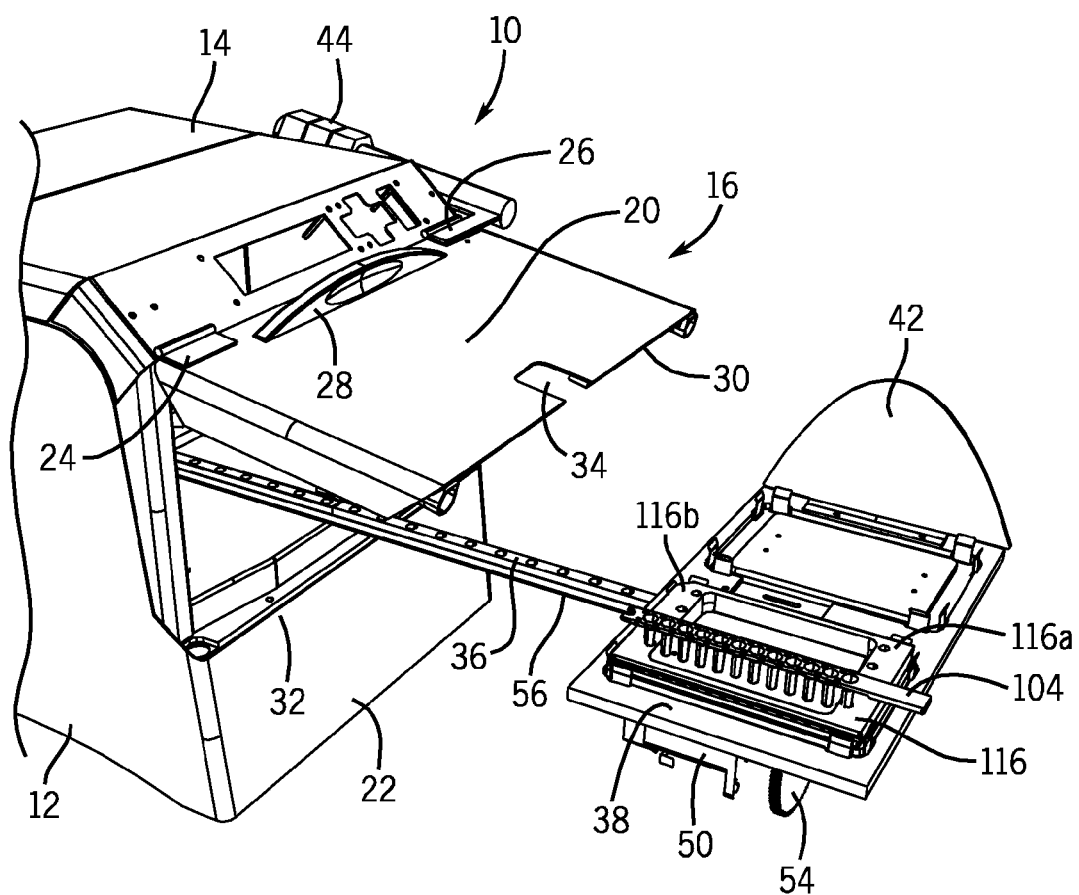
FIG. 2 is a perspective view illustrating one side of the magnetic particle processor. In this figure, a tray for supporting a tip comb rack for inserting a tip comb in the magnetic particle processor is shown.

Referring now to FIGS. 2, 16, and 17, the tip comb platform 112 can be loaded with tip combs 104 by means of tip comb racks 116 (see FIG. 2), which can be used to load and unload tip combs 104 (see FIGS. 2, 16, 17) as the supporting tray 38 for the micro-well plate(s) 40 moves into and out of the magnetic particle processor 10. The magnetic particle processor 10 comprises the same or a substantially similar processing head with tip combs and magnetic rods as shown in the magnetic particle processor shown in FIG. 16. As indicated with respect to FIG. 16, the processing head consists of two vertically moving platforms. One platform is needed for the magnetic rods (2×12 rods) and the other platform is needed for the plastic tip combs 104. The position of a tip comb slot of the tip comb platform of the magnetic particle processor 10 is coordinated with the tip comb movements of the tip comb racks 116.

Clean tip combs (typically four in number) reside in a clean tip comb rack 116 that maintains the tip combs 104 in an upright orientation and properly aligned for insertion into the slot 112a in the tip comb platform 112. See FIG. 2 for the tip comb rack and FIG. 16 for the tip comb platform 112 and the slot 112a. A clean tip comb rack 116 is placed onto the supporting tray 38 in a manner similar to that used to insert a micro-well plate onto the supporting tray 38, i.e., by means of a XYZ aspirating/dispensing device equipped with gripping devices. The tip comb platform 112 (located in the interior of the magnetic particle processor 10) is lowered and aligned with the end of the tip comb 104 to be loaded. The supporting tray 38 is then transported into the magnetic particle processor 10 and the tip comb 104 is simultaneously inserted into the tip comb platform 112. The supporting tray 38 is designed to keep the clean tip comb rack 116 in registration with the tip comb platform 112 and to counteract the friction/slip force required to load the tip comb onto the tip comb platform 112. Then the tip comb platform 112 is raised and the supporting tray 38 is transported out of the magnetic particle processor 10. This step is referred to as a "tip comb insertion step." The tip comb platform 112 and the three tip combs 104 that are not aligned with the slot 112a would collide when the supporting tray 38 is inserted into the magnetic particle processor 10 unless the innermost tip comb 104 is inserted first, because the slot 112a is positioned near the left end of the front of the tip comb platform 112. Therefore, the innermost tip comb 104, i.e., the tip comb closest to the center of the magnetic particle processor 10 is inserted into the slot 112a first. Then the clean tip comb rack 116, along with the remaining three tip combs 104 in the clean tip comb rack 116, are removed and placed in a holding area for the next loading operation. This step is referred to as a "tip comb rack holding step." After the first set of assays is carried out, the innermost tip comb 104 is removed by a used tip comb rack 116 for used tip combs 104. To remove a used tip comb 104, the tip comb platform 112 is merely lowered, thereby lowering the used tip comb 104 in such a manner that the tips 104a at the two ends of the tip comb 104 enter the slots 116a, 116b in the used tip comb rack 116. Then the supporting tray 38 is transported out of the magnetic particle processor 10 and the used tip comb rack 116 is placed in a temporary storage area by the XYZ aspirating/dispensing device, equipped with gripping devices. This step is referred to as a "tip comb removal step." The aforementioned clean tip comb rack 116 is retrieved by the XYZ aspirating/dispensing device, which is equipped with gripping devices, and the tip comb insertion step, another set of assays, and the tip comb removal step are carried out with the tip comb 104 that was immediately adjacent to the innermost tip comb 104. The tip comb rack holding step is carried out with the two remaining tip combs. After the second set of assays is carried out, the tip comb 104 just used is removed by the aforementioned used tip comb rack 116 and stored in the manner described previously. Then the aforementioned clean tip comb rack 116 is again retrieved by the XYZ aspirating/dispensing device, equipped with gripping devices, and the tip comb insertion step, another set of assays, and the tip comb removal step are carried out with the tip comb 104 that was immediately adjacent to the tip comb 104 that had been immediately adjacent to the innermost tip comb 104. The tip comb rack holding step is carried out with the one remaining tip comb. After the third set of assays is carried out, the tip comb 104 just used, i.e., the third tip comb 104, is removed by the aforementioned used tip comb rack 116 and stored in the manner described previously. Then the aforementioned clean tip comb rack 116 is again retrieved by the XYZ aspirating/ dispensing device, equipped with gripping devices, and the tip comb insertion step, another set of assays, and the tip comb removal step are carried out for the tip comb 104 that was furthest from the innermost tip comb 104. At this point, the four tip combs 104 in the tip comb rack 116 have been used, the used tip comb rack 116 is used to remove the last-mentioned used tip comb 104, and the used tip comb rack 116 containing these used tip combs 104 is disposed in a solid waste container.

As can be understood from the foregoing discussion, unloading the used tip combs 104 involves reversing the insertion process, with the only exception being that the used tip combs 104 are maintained separate from the clean tip combs 104 and a filled used tip comb rack 116, which contains four used tip combs 104 is disposed of into a solid waste container (not shown). The tip comb racks 116 containing used tip combs 104 are separated from the tip comb racks 116 containing clean tip combs 104, so that the used tip combs 104 do not contaminate the clean tip combs 104. The required control synchronization can be performed by means of the RS-232 interface on the magnetic separation and mixing subsystem, and by means of the USB interface on the XYZ aspirating/dispensing device. Tip combs 104 can be automatically loaded and unloaded by means of gripping devices on the pipettes of the XYZ aspirating/dispensing device. These gripping devices will be described later.

Figure 3:
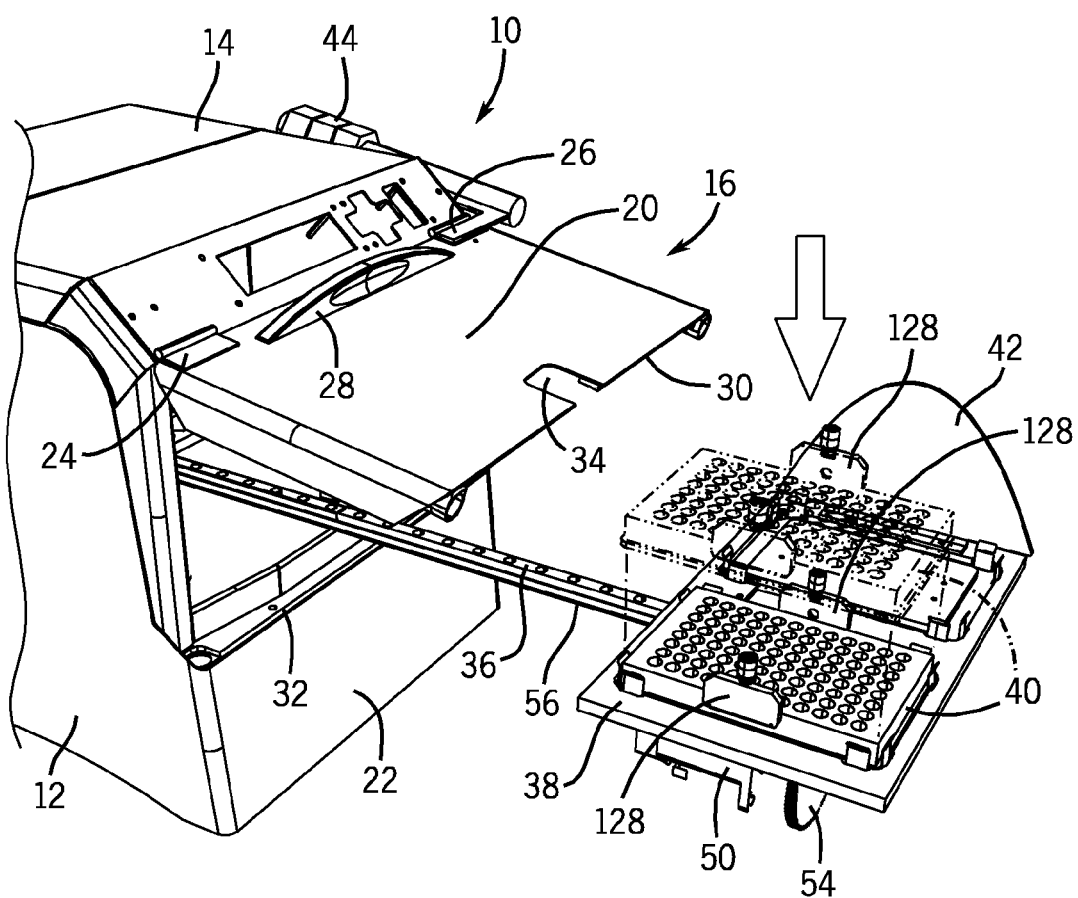
FIG. 3 is a perspective view illustrating the same side of the magnetic particle processor as shown in FIG. 2. In this figure, a tray for supporting a micro-well plate is shown fully extended from the magnetic particle processor.

Referring now to FIG. 3, dispensing of liquids into the micro-wells in a micro-well plate 40 can be performed without removing the micro-well plate 40 from the supporting tray 38. This feature can be used to enable the performance of homogeneous assays in a magnetic particle processor. A homogeneous assay does not require separation steps. The required control synchronization can be performed by means of the RS-232 interface on the magnetic separation and mixing subsystem, and by means of the USB interface on the XYZ aspirating/dispensing device. Protocols for dispensing liquids by the XYZ aspirating/dispensing device can be automatically interleaved with magnetic separation and mixing.

The components of the system can be controlled by a personal computer using various, available interfaces. These interfaces are identified in FIG. 1. The operations of the magnetic particle processor 10 can be controlled by a personal computer, using commercially available interfaces, which are also identified in FIG. 1. The graphical user interface can use features and controls that are common to modern personal computer graphical user interfaces. For example, drop down menus and tree-views can be used for multiple choices. Radio buttons, checkboxes, and slider controls can provide selection options that are intuitive to the operator. Splash screens, progress bars, and highlighted controls can provide status reports that are intuitive to the operator. Hotlinks can provide access to web sites or local information such as help, maintenance procedures, training, etc.

The graphical user interface can be provided with the capability to make views semi-transparent to prevent views at the top of the screen from completely obscuring views underneath. The graphical user interface can be provided with the capability to zoom in or zoom out to provide details for selected items, rather than requiring the operator to select a lower level "details screen". The graphical user interface can be provided with widgets to allow the operator to move small windows around the screen for customizing displays (such as a clock, or test counter, etc.). The graphical user interface can be provided with the capability to view and interact with a graphical depiction of the instrument. The area under a cursor can be highlighted and/or magnified for selection, information, zoomed viewing, etc. The graphical user interface can have instructional pop-up balloons for providing details and/or information for selected items, rather than requiring the operator to select a lower level "details screen" or "help screen". The graphical user interface can be equipped with fuel gauge-type icons to quickly indicate low levels of consumable items and/or reagents. A touch screen can be used to allow an alternative for a keyboard and/or a mouse.

The operator or a Laboratory Information System (LIS) will download test orders to the system, for samples that will eventually be presented to the system for testing.

The operator or a Laboratory Automation System (LAS) will load the required consumable items onto the system. The operator or the Laboratory Automation System will present the required samples to the system. The system will determine and report the analyte (i.e., antigen or antibody) in a sample, according to the downloaded test order for that sample. The operator or the Laboratory Automation System will remove the samples from the system. The operator or the Laboratory Information System will review/release test results to the origin of the test order.

The Laboratory Automation System, which comprises the subsystem described herein, automatically dispenses liquids, loads tip combs, and loads micro-well plates onto the system for the various processing step(s) and the incubation step(s) required for magnetic separation of a solid magnetic substrate from the liquid contents of a reaction vessel, i.e., micro-wells. After processing, the system will automatically unload used tip combs and used micro-well plates.

The Laboratory Automation System can determine/report the analyte/antigen in a sample, according to the downloaded test order for that sample. The operator or the Laboratory Automation System will remove the samples from the system. The operator or the Laboratory Information System will review/release test results to the origin of the test order.

During the magnetic particle processing operation, the rotatable upper portion 20 and the top panel 14 of the magnetic particle processor 10 can be closed or can remain open. Closed lids protect the processing against environmental contamination and loss of heat.

It should be noted that the apparatus described herein is not limited for use with immunoassays. The assay described herein can be used with any assay that involves the separation of magnetic microparticles. Other assays involving the separation of magnetic microparticles are described in U.S. patent application Ser. No. 12/257,495, which has been filed as a non-provisional United States Patent Application on Oct. 24, 2008, and which claims priority from U.S. Provisional Application Ser. No. 60/985,373, filed Nov. 5, 2007, entitled AUTOMATED ANALYZER FOR CLINICAL LABORATORY, and furthermore, is incorporated herein by reference, describes extraction of nucleic acids from biological samples.

A KingFisher™ Flex magnetic particle processor can be used for extraction of nucleic acids from biological samples. A substantially similar embodiment of the magnetic particle processor as was described with respect to FIGS. 12, 13, 14, and 15 can be used for the kitting of multi-well plates and magnetic particle processing.

The KingFisher™ Flex magnetic particle processor can provide rapid and reproducible purification of high-quality DNA, RNA, proteins, and cells from various starting materials, such as, for example, blood, cell cultures, tissue lysates, soil, and faeces. Like the KingFisher™ magnetic particle processors described previously, the KingFisher™ Flex magnetic particle processor uses magnetic rods that move particle through the various purification phases, i.e., binding, missing, washing, elution. The KingFisher™ Flex magnetic particle processor uses a 24-rod magnet head and 24-well deep well plate. The volume of sample can be as high as 5 mL. For higher throughput needs, 96 samples can be processed in different working volumes (20-1000 μL) using 96-rod magnet head and appropriate 96-well plates. Additional details relating to the KingFisher™ Flex magnetic particle processor is accessible by means of the Hypertext Transfer Protocol on the World Wide Web at the website thermo.com/com/cda/product/detail/1,,10136240,00.html, incorporated herein by reference.

FIGS. 12, 13, 14, and 15 illustrate an apparatus that can accommodate multi-well plates to be kitted for extraction of a nucleic acid from a sample. Referring now to FIGS. 12, 13, 14, and 15, each deep well plate for extraction of a nucleic acid, such as, for example, RNA (1.0 mL HIV) encompasses an entire step of the protocol for the magnetic particle processor. Thus, one complete deep well multi-well plate can used for the introduction of samples along with microparticles and appropriate buffer, two complete deep well multi-well plates can be used for diluted lysis buffer, two complete deep well multi-well plates can be used for water, and one complete deep well multi-well plate can be used for phosphate buffer. A total of six deep well multi-well plates can be used for a given magnetic separation process for the aforementioned antigen. After the samples, the magnetic microparticles, and the buffers are introduced to the deep well multi-well plates and the appropriate incubation procedures have been carried out, the deep well multi-well plates are transferred to a KingFisher™ Flex magnetic particle processor. Additional details relating to extraction of RNA from biological samples can be found in U.S. patent application Ser. No. 12/257,495, which has been filed as a non-provisional United States Patent Application on Oct. 24, 2008, and which claims priority from U.S. Provisional Application Ser. No. 60/985,373, filed Nov. 5, 2007, entitled AUTOMATED ANALYZER FOR CLINICAL LABORATORY, and furthermore, is incorporated herein by reference. Furthermore, details relating to extraction of DNA from biological samples can be found in U.S. patent application Ser. No. 12/257,495, which has been filed as a non-provisional United States Patent Application on Oct. 24, 2008, and which claims priority from U.S. Provisional Application Ser. No. 60/985,373, filed Nov. 5, 2007, entitled AUTOMATED ANALYZER FOR CLINICAL LABORATORY, and furthermore, is incorporated herein by reference.

The sample is typically serum. Serum is typically used in both immunoassay analyzers and clinical chemistry analyzers. Other samples, such as, for example, sputum or tissue scrapings, will be eluted in a volume of liquid that would be equivalent to a volume of serum. The lysis buffer disrupts cell membranes and exposes nucleic acid. A representative example of lysis buffer suitable for use herein (RNA) comprises a mixture of 4.66M guanidine isothiocyanate, 2-amino-2-(hydroxymethyl)-1,3-propanediol (Trizma®, pH 8.0), and polyoxyethylenesorbitan monolaurate (Tween® 20, 10%). A representative example of diluted lysis buffer suitable for use herein comprises 2M guanidine isothiocyanate, polyoxyethylenesorbitan monolaurate (Tween® 20, 5%), and 50 mM potassium acetate (pH 6.0). A representative example of a phosphate buffer suitable for use herein comprises 20 mM potassium phosphate (pH 8.5). The nucleic acid then attaches to magnetic microparticles. Magnetic microparticles are typically particles of iron oxide.

TABLE 1 lists the materials, amounts, time and temperature conditions for each deep well of the multi-well plate, and an approximate time for kitting. The table also lists the figure that illustrates the deep well multi-well plate.

TABLE 1

| Multi-well plate | Material in each well | Quantity of material (μL) | Temperature (°C.) | Time (minutes) | Time for kitting (minutes) |
|---|---|---|---|---|---|
| 1 | Magnetic microparticles | 100 | 50 | 20 | 14.5 |
| 1 | Lysis buffer | 2400 | 50 | 20 | 14.5 |
| 1 | Sample | 1000 | 50 | 20 | 14.5 |
| 2 | Diluted lysis buffer | 700 | 25 | | 1 |
| 3 | Diluted lysis buffer | 700 | 25 | | 1 |
| 4 | Water | 700 | 25 | | 1 |
| 5 | Water | 700 | 25 | | 1 |
| 6 | Phosphate buffer* | 25 | 75 | 20 | 2 |

*Water (63 μL) is added to each well of the multi-well plate prior to the step of transferring the extracted nucleic acid to the wells of a PCR plate.

The lysis buffer disrupts cell membranes, thereby exposing nucleic acid and enabling the nucleic acid to attach to magnetic microparticles. The material in the multi-well plates (not shown), i.e., diluted lysis buffer, water, operate to wash away the lysis buffer, because the lysis buffer interferes with the polymerase chain reaction for amplifying nucleic acids. The phosphate buffer elutes, i.e., releases the nucleic acid from the magnetic microparticles.

A high-speed reagent dispenser can be employed to kit the multi-well plates 2-6 at the same time that the multi-well plate 1 is being kitted by a different dispensing device, in which case a saving of 5.5 minutes of kitting time can be realized.

After the nucleic acid is released form the magnetic microparticles, the nucleic acid can be aspirated from the deep wells of the multi-well plate and transferred to the wells of a 96-well PCR plate. This transfer step is referred to herein as master mixing and activating. An example of the transfer step involves the transfer of samples from four magnetic particle processing operations from one or more KingFisher™ Flex magnetic particle processors to the 96-well PCR plate. After the samples that have been processed by the magnetic particle processor have been introduced to the 96-well PCR plate, the appropriate reagents are introduced to each well of the 96-well PCR plate, the 96-well PCR plate is sealed, and the sealed 96-well PCR plate is transferred to the thermal cycler for further processing.

The amplification of the nucleic acid can be carried out in a thermal cycler, also known as a thermocycler, PCR machine, or DNA amplifier. This device can be used to amplify segment of DNA via the polymerase chain reaction (PCR) process. The device has thermal block with holes where tubes holding the PCR reaction mixtures can be inserted. The cycler then raises and lowers the temperature of the block in discrete, pre-programmed steps. Thermal cyclers are described, for example, in articles, such as, for example, Thermal cycler, which is accessible by means of the Hypertext Transfer Protocol at the website en.wikipedia.org/wiki/Thermal_cycler, incorporated herein by reference. Additional information relating to the processes carried out by thermal cyclers can be found, for example, in articles, such as, for example, Polymerase chain reaction, which is accessible by means of the Hypertext Transfer Protocol at the website en.wikipedia.org/wiki/Polymerase_chain_reaction, incorporated herein by reference. Representative examples of thermal cyclers suitable for use herein include ABI7500 Thermocycler/Reader, Bio-Rad® i-Cycler®, Stratagene MX4000™.

The estimated processing time for the KingFisher™ Flex magnetic particle processor is 44 minutes. The estimated time for thermal cycling and reading is three hours. The estimated time for master mixing and activating is 32 minutes. The estimated time for achieving the first result is approximately four hours and 46 minutes. The approximate throughput is 94 tests per hour.

OPERATION

In order to rotate the rotatable upper portion 20 to obtain access to the interior of the magnetic particle processor 10, the motor 50 is switched on. The shaft of the motor 50 drives the drive gear 54 in a clockwise direction (either clockwise or counterclockwise), thereby driving the driven gear 58. The driven gear 58 causes the threaded lead screw 56 to rotate in the appropriate clockwise direction (either clockwise or counterclockwise), thereby causing the threaded nut to cause the supporting tray 38 to move in a direction along the supporting rail 36 away from the magnetic particle processor 10. The cam 42 attached to the supporting tray 38 contacts the interior wall of the rotatable upper portion 20, which results in the rotation of the rotatable upper portion 20 so as to enable the supporting tray 38 to emerge from the magnetic particle processor 10. As the rotatable upper portion 20 rotates outwardly away from the magnetic particle processor 10, the counterweight 44 rotates in the same direction as does the rotatable upper portion 20. When the rotatable upper portion 20 has rotated to its maximum extent, the rotatable upper portion 20 is stabilized in the open position by the gravitational force of the counterweight 44.

Referring now to FIG. 2, the supporting tray 38 is shown in the fully extended position. When the supporting tray 38 is in this position, the rotatable upper portion 20 is in the open position, and the counterweight maintains the rotatable upper portion 20 in the open position.

Figure 19:
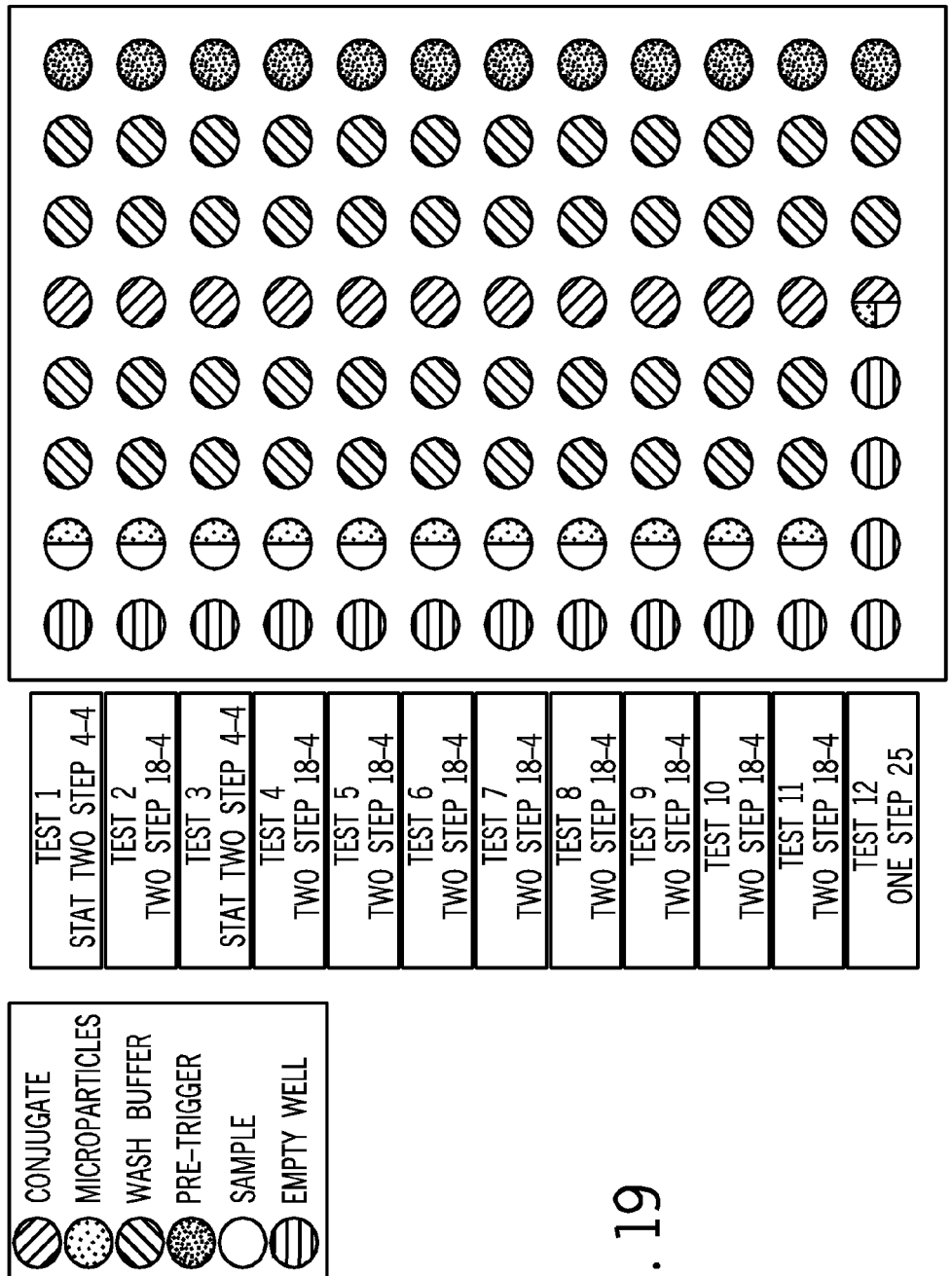
FIG. 19 is a top plan view of a micro-well plate illustrating the kitting of chemiluminescent microparticle immunoassays utilizing a single micro-well plate having 96 micro-wells.

When the supporting tray 38 is fully extended, a tip comb 104 is inserted into the slot 112a of the tip comb platform 112 in the manner described previously. Then a micro-well plate 40 is placed into position on the supporting tray 38 in the manner described previously. As indicated previously, retrieving tip comb racks 116 and retrieving micro-well plates 40 are carried out by means of a first gripping device 128 attached to the stem of the first 126 of two pipettes of an XYZ aspirating/dispensing device and a second gripping device 128 attached to the stem of the second 126 of two pipettes of the XYZ aspirating/dispensing device. The resilient clips 64a, 64a', 64b, 64b', 64c, 64c', and 64d, 64d' ensure that the micro-well plate 40 is securely attached to the supporting tray 38. When properly positioned, the micro-well plate 40 is in contact with the upraised portion 66 of the supporting tray 38 whereby satisfactory incubation of reaction mixtures can be carried out. Such reaction mixtures are shown, for example, in FIG. 19. FIG. 19 illustrates the kitting of chemiluminescent microparticle immunoassays utilizing a single micro-well plate having 96 micro-wells. Incubation of the sample and the magnetic microparticles are performed in the second row of the micro-well plate. Wash buffer is dispensed in the third, fourth, sixth, and seventh rows of the micro-well plate. The conjugate is dispensed in the fifth row of the micro-well plate. Pre-trigger solution is dispensed in the eighth row of the micro-well plate.

For immunoassays employing inverse magnetic particle processing, the micro-well plate 40 has already been kitted with samples, reagents, conjugates, pre-trigger solution, wash buffer, etc., in a kitting area, distinct from the magnetic particle processor 10. Such kitting is described in greater detail in co-pending application U.S. patent application Ser. No. 12/257,495, which has been filed as a non-provisional United States Patent Application on Oct. 24, 2008, and which claims priority from U.S. Provisional Application Ser. No. 60/985,373, filed Nov. 5, 2007, entitled AUTOMATED ANALYZER FOR CLINICAL LABORATORY, and incorporated herein by reference.

Figure 4:
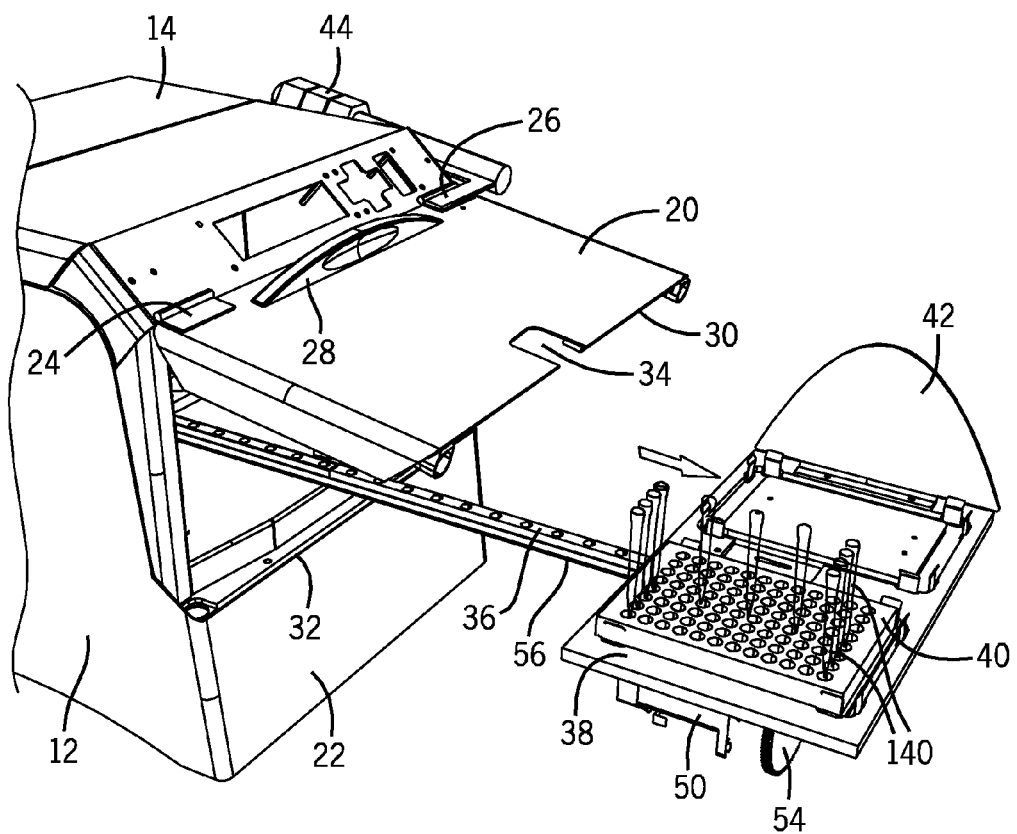
FIG. 4 is a perspective view illustrating same side of the magnetic particle processor as shown in FIG. 2. In this figure, a tray for supporting a micro-well plate is shown fully extended from the magnetic particle processor. Pipette tips are shown dispensing either samples or reagents into micro-wells of a micro-well plate on the supporting tray.

Referring to FIG. 4, in the case of homogeneous immunoassays, where magnetic particle processing is not necessary, samples and reagents can be introduced to micro-wells of micro-well plates 40 by means of pipettes equipped with pipette tips. As can be seen in FIG. 4, a plurality of pipette tips 140 is in register with the micro-wells of a micro-well plate 40.

In order to rotate the rotatable upper portion 20 to close the front panel 16 of the magnetic particle processor 10, the direction of the motor 50 is reversed. The shaft of the motor 50 drives the drive gear 54 in the clockwise direction opposite to that used to open the rotatable upper portion 20, thereby driving the driven gear 58. The driven gear 58 causes the threaded lead screw 56 to rotate in the clockwise direction opposite to that rotated by the threaded lead screw 56 when the rotatable upper portion 20 was opened, thereby causing the threaded nut to cause the supporting tray 38 to move in a direction along the supporting rail 36 toward the magnetic particle processor 10. The cam 42 attached to the supporting tray 38 contacts the cam follower 48, which results in the rotation of the counterweight 44 in the clockwise direction opposite to that rotated by the threaded lead screw 56 when the rotatable upper portion 20 was opened so as to enable the rotatable upper portion 20 to close as the supporting tray 38 enters the magnetic particle processor 10. As the counterweight 44 rotates, the rotatable upper portion 20 rotates in the same direction as does the counterweight 44. When the counterweight 44 has rotated to its maximum extent, the rotatable upper portion 20 is stabilized in the closed position by the force of the cam follower 48, which prevents the cam 42 from moving. Furthermore, when the counterweight 44 is in the vertical position, as shown, for example, in FIG. 5, the weight thereof is not able to cause the rotatable upper portion 20 to rotate.

Figure 5:
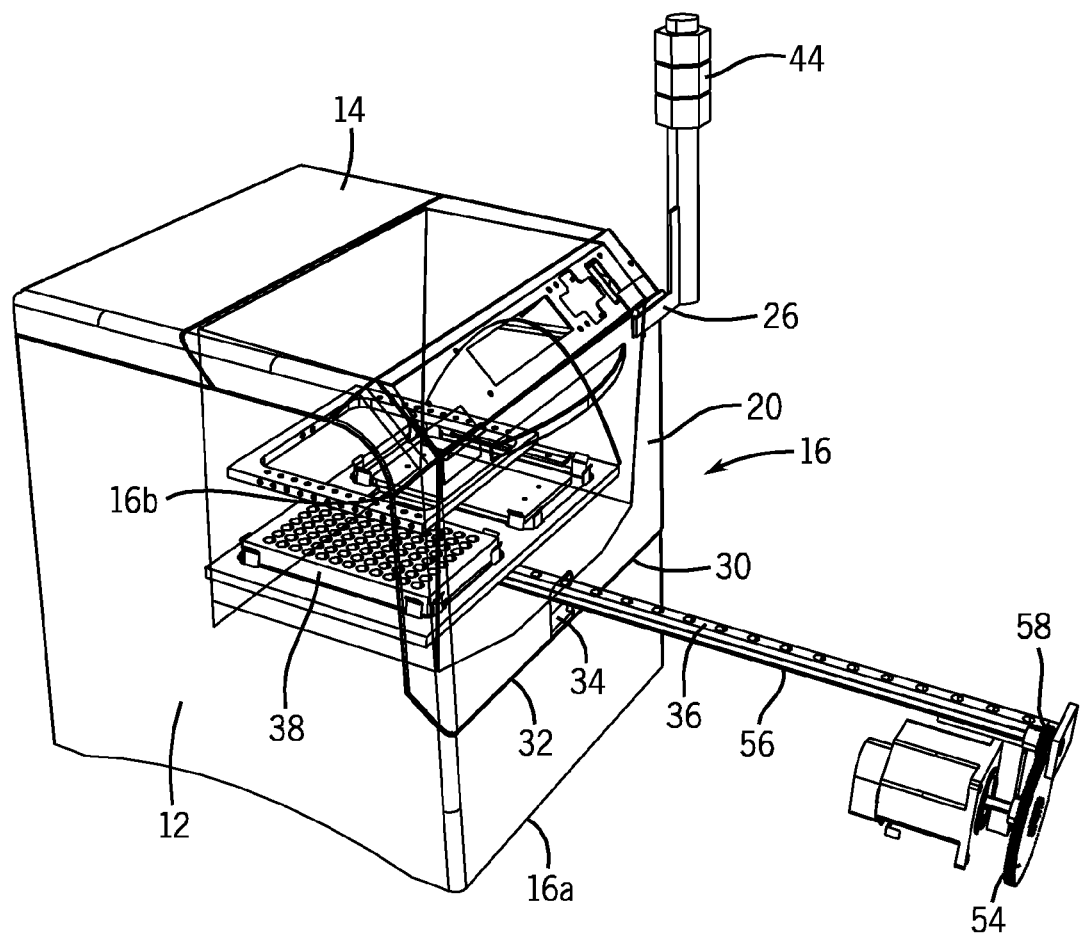
FIG. 5 is a perspective view illustrating the same side of the magnetic particle processor as shown in FIG. 2. In this figure, a tray for supporting a micro-well plate is shown inserted into the magnetic particle processor.

Referring now to FIG. 5, the supporting tray 38 is completed enclosed within the magnetic particle processor 10. When the supporting tray 38 is in this position, the rotatable upper portion 20 is in the closed position, and the cam follower 48 prevents the counterweight 44 from inducing the rotatable upper portion 20 into the open position.

It should be noted that the samples and the reagents are dispensed into the micro-wells of the micro-well plate 40 at a kitting station, separate from the magnetic particle processor 10. The sample(s), the reagent(s), the buffer(s), and the other materials (e.g., the pre-trigger solution) are added at the kitting station.

When the supporting tray 38 carrying the micro-well plate 40 is in the magnetic particle processor 10, the reaction mixtures, and other liquids, are incubated by means of the heater pads 68a, 68b. After the required incubation steps, the reaction mixtures are processed by means of the magnetic particle processor 10 in order to separate solid magnetic substrate from the liquid contents of the micro-wells. After the placement of the micro-well plates 40 has been completed, the inverse magnetic particle processing operation is carried out. When that processing has been completed, the results derived from the processing are performed by a reader (not shown), e.g., a luminometer in the case of a chemiluminescent microparticle immunoassay. The micro-well plate from which readings are taken is transferred to the reader by means of the XYZ aspirating/dispensing device and any other transfer equipment required, such as, for example, a conveyor belt (not shown) or a robotic mechanism (not shown). The micro-well plates 40 remaining are removed by the XYZ aspirating/dispensing device one at a time and disposed of in a solid waste container (not shown).

In order to operate the magnetic particle processor 70 derived from the KingFisher™ 96 magnetic particle processor, a signal is provided by a pulse generator, such as, for example, a square wave pulse generator associated with a stepper motor driver to actuate the motor 82 to move the movable plate 78. A micro-well plate 40 is retrieved by the XYZ aspirating/dispensing device from a storage rack (not shown). The micro-well plate 40 is placed in position in the magnetic particle processor 70. This placement of micro-well plate step is repeated for up to seven more micro-well plates 40. For a given micro-well plate 70, each micro-well contains the same component for inverse magnetic particle processing. For example, kitting micro-well plates for the magnetic particle processor 70 derived from the KingFisher™ 96 magnetic particle processor is carried out a location separate from the magnetic particle processor 70. As stated previously, the samples and the reagents are dispensed into the micro-wells of the micro-well plates 40 at a kitting station, separate from the magnetic particle processor 10. The sample(s), the reagent(s), the buffer(s), and the other materials (e.g., the pre-trigger solution) are added at the kitting station. After the placement of the micro-well plates 40 has been completed, the inverse magnetic particle processing operation is carried out. When the turntable 76 carrying the micro-well plates 40 are in the magnetic particle processor 70, the reaction mixtures, and other liquids, are incubated by means of the heater pads 68, 68. After the required incubation steps, the reaction mixtures are processed by means of the magnetic particle processor 70 in order to separate solid magnetic substrate from the liquid contents of the micro-wells. When that processing has been completed, the results derived from the processing are performed by a reader (not shown), e.g., a luminometer in the case of a chemiluminescent microparticle immunoassay. The micro-well plate from which readings are taken is transferred to the reader by means of the XYZ aspirating/dispensing device and any other transfer equipment required, such as, for example, a conveyor belt (not shown) or a robotic mechanism (not shown). The micro-well plates 40 remaining are removed by the XYZ aspirating/dispensing device one at a time and disposed of in a solid waste container (not shown).

The aspirating/dispensing device has a head that can be equipped with a plurality of pipettes 126. A commercially available robotic system suitable for use herein typically has from four to twelve pipettes. The gripping devices 128 are capable of gripping reagent containers, sample containers, and micro-well plates, raising the gripped container or the gripped micro-well plate in a vertical direction, and lowering the gripped container or the gripped micro-well plate in a vertical direction. The aspirating/dispensing device is capable of moving in the two horizontal directions that are perpendicular to one another. The range of movement in either direction is unlimited. However, for the sake of economics, it is preferred that the analysis sections be as small as possible. Accordingly, it is expected that a typical range of movement for the aspirating/dispensing device be from about two feet to about eight feet, preferably from about two feet to about six feet, more preferably from about two feet to about four feet in both horizontal directions. A robotic system suitable for use with the apparatus and method described herein is commercially available from Hamilton Company. In this system, two pipettes 126 of the aspirating/dispensing device are capable of receiving the gripping devices 128. The gripping devices 128 can be securely attached to the stems of the pipettes 126 of the aspirating/dispensing device by means of an expandable O-ring locking mechanism. The expandable O-ring locking mechanism is described in U.S. Pat. No. 7,033,543, incorporated herein by reference.

Figure 20E:
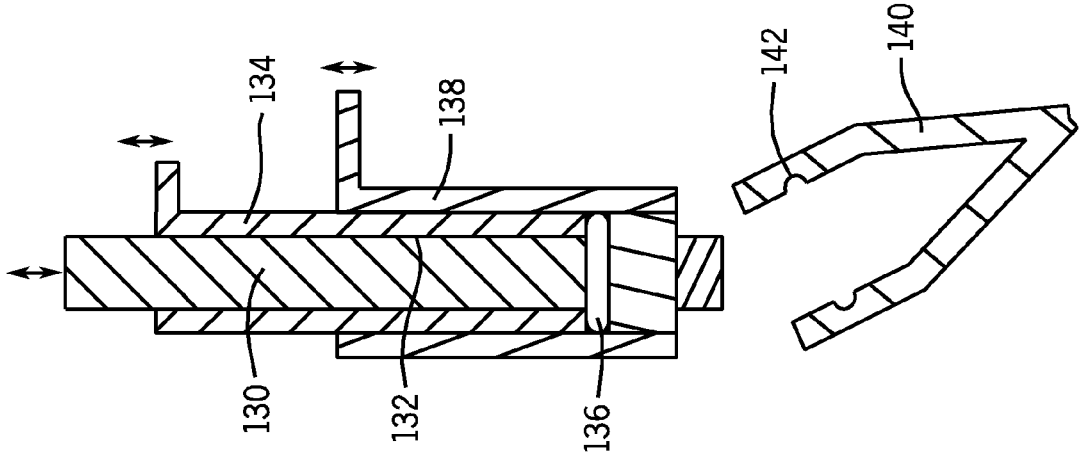
Figure 20D:
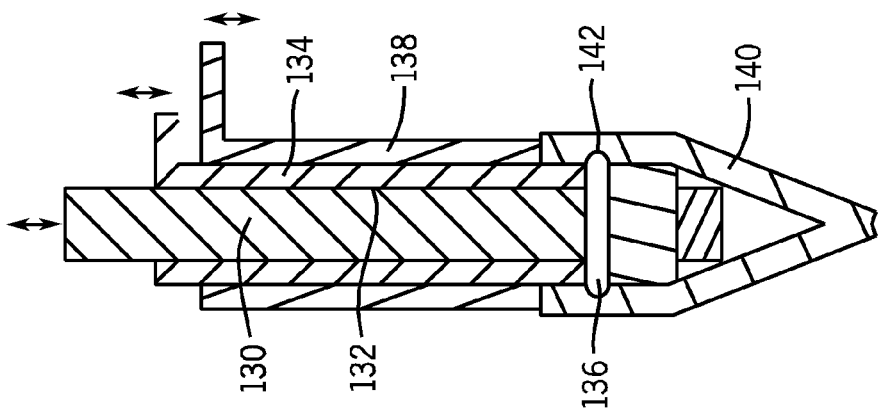

FIGS. 20A, 20B, 20C, 20D, and 20E illustrate the operation of the expandable O-ring locking mechanism. The pipette 126 comprises a cylindrical tube having an interior wall 130 and an exterior wall 132. Encircling a significant portion of the exterior wall 132 of the pipette 126 is an O-ring actuator sleeve 134. An expandable O-ring 136 is positioned around the exterior wall 132 of the pipette 126 and immediately below the lower end of the O-ring actuator sleeve 134. The expandable O-ring 136 is typically made from a resilient polymeric material. Encircling a significant portion of the O-ring actuator sleeve 134 is an ejector sleeve 138. In FIG. 20A, neither a gripping device 128 nor a pipette tip 140 is mounted to the pipette 126. In FIG. 20B, either a gripping device 128 or a pipette tip 140 is mounted to the pipette 126 by means of a slip fit, wherein there is little or no insertion force. In FIG. 20C, the expandable O-ring 136 is compressed and expanded by means of the O-ring actuator sleeve 134, which is moved vertically by a small motor (not shown). In FIG. 20D, the gripping device 128 or the pipette tip 140 is locked onto the cylindrical tube of the pipette 126 via the expandable O-ring 136 and a groove 142 in the interior wall of the pipette tip 140. In FIG. 20E, the expandable O-ring 136 is decompressed and retracted radially by raising the O-ring actuator sleeve 134, by reversing the direction of the aforementioned motor. The gripping device 128 or the pipette tip 140 is removed for disposal or reuse by means of the ejector sleeve 138, which is moved relative to the main tube of the pipette by a small motor (not shown).

The gripping devices 128 are typically rectangular parallelepipeds, e.g., in the shape of paddles, and are typically made of metal, e.g., stainless steel. FIGS. 10A and 10B illustrate gripping devices 128 that are suitable for gripping micro-well plates. Each paddle-shaped gripping device 128 has at least one projection, preferably two or more projections, on the major surface thereof that contacts the edge of a micro-well plate. When the paddle-shaped gripping devices 128 are affixed to pipettes 126, the paddle-shaped gripping devices 128 are retained by expandable O-rings 136 described previously. As mentioned previously, this same expandable O-ring 136 can be used to retain a pipette tip 140, which can be slipped over the discharging end of a pipette 126. This expandable O-ring mechanism holds the pipette tip securely, while the pipette is being used to aspirate and dispense fluids and even when the pipette tip is penetrating the septum of a container, which activity would typically cause a friction-staked pipette tip to be pulled off the discharging end of the pipette.

In order for the aspirating/dispensing device to grip a micro-well plate, two pipettes of the aspirating/dispensing device to which the gripping devices 128 are attached are moved toward each other, whereby the micro-well plate can be gripped between the paddle-shaped gripping devices 128. When being gripped, the micro-well plate can be either in the portrait or landscape orientation, i.e., the micro-well plate can be gripped via either the two longer sides of the micro-well plate or by the two shorter sides of the micro-well plate. The projections mentioned previously penetrate slightly into the surface of the soft plastic material of the micro-well plate, thereby securely holding the micro-well plate for raising, lowering, or transporting.

The apparatus and method described herein enables the automatic loading and unloading of micro-well plates by interfacing with a XYZ aspirating/dispensing device. The apparatus and method described herein enables the automatic loading and unloading of tip combs by interfacing with a XYZ aspirating/dispensing device. The apparatus and method described herein enables integration of incubation functions with magnetic separation and mixing functions. The apparatus and method described herein enables protocol changes by interfacing with a XYZ aspirating/dispensing device and allowing dispensing of liquids to be interleaved with magnetic separation and mixing operations.

The apparatus described herein facilitates automation of loading and unloading of micro-well plates. The apparatus described herein facilitates automation of loading and unloading tip combs into a magnetic particle processor.

The apparatus and method described herein enables the combination of separating a solid magnetic substrate from the liquid contents of a reaction vessel with incubation.

The apparatus and method described herein enables the required control synchronization to be performed via the RS-232 interface on the magnetic separation and mixing subsystem, and the USB interface on the XYZ aspirating/dispensing device.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A system comprising:
   a magnetic particle processor;
   a multi-well plate;
   a tip comb;
   a movable interface;
   a tip comb rack to support the tip comb;
   a tip comb platform disposed in the magnetic particle processor;
   a transfer device to at least one of dispense contents into or aspirate contents from the multi-well plate;
   a heater thermally coupled to the movable interface to incubate the contents in the multi-well plate;
   a resistive temperature detector to regulate a temperature of the heater; and
   a controller to control the movable interface to automatically:
      load the tip comb into the tip comb platform by inserting the tip comb rack with the tip comb into the magnetic particle processor and unload the tip comb from the tip comb platform by removing the tip comb rack with the tip comb from the magnetic particle processor; and
      load the multi-well plate into the magnetic particle processor and unload the multi-well plate from the magnetic particle processor.

2. The system of claim 1, wherein the contents of the multi-well plate include at least one of an unbound sample, an unbound conjugate, a wash buffer or a pre-trigger solution.

3. The system of claim 1, wherein the contents of the multi-well plate include a biological sample and at least one reagent for extracting a nucleic acid from the biological sample.

4. The system of claim 1, wherein the transfer device is movable in three dimensions.

5. The system of claim 1, wherein the controller is to synchronize the magnetic particle processor and the transfer device.

6. The system of claim 1, wherein the movable interface comprises a tray to support the multi-well plate.

7. The system of claim 6 further comprising a driver to drive the tray into and out of the magnetic particle processor to load the multi-well plate.

8. The system of claim 1 further comprising a mixer to mix the contents of the multi-well plate including a sample with a reagent.

9. The system of claim 1, wherein the magnetic particle processor comprises a magnetic rod and when the tip comb is inserted into the tip comb platform, the tip comb is to cover at least a portion of the magnetic rod, wherein the multi-well plate includes a plurality of wells and the contents of a first well includes a plurality of magnetic microparticles, and wherein the magnetic rod is to collect at least some of the plurality of microparticles onto the tip comb and transfer the at least some of the plurality of microparticles to a second well.

10. The system of claim 9, wherein the tip comb includes a strip of non-magnetic material.

11. The system of claim 1 further comprising insulation to regulate a temperature of the magnetic particle processor.

12. The system of claim 1 further comprising an antenna to read a radio frequency identification tag attached to the multi-well plate.

13. The system of claim 1, wherein the magnetic particle processor comprises a turntable.

14. The system of claim 13, wherein the turntable is to support a plurality of multi-well plates and the magnetic particle processor is to perform ninety-six immunoassays simultaneously.

15. The system of claim 14, wherein each of the plurality of multi-well plates includes a plurality of wells and each of the plurality of wells on one of the multi-well plates contains the same reagent or the same mixture of sample and reagent.

16. The system of claim 1, wherein the multi-well plates are micro-well plates.

17. The system of claim 1,
   wherein the movable interface comprises a resilient supporting clip to secure the multi-well plate, and the clip includes a bevel to adjust a position of the multi-well plate.

18. The system of claim 1 further comprising a track along which the movable interface traverses.

19. The system of claim 1 further comprising:
   a cam coupled to the movable interface;
   a cam follower operatively coupled to a rotatable hatch, wherein as the movable interface moves into the magnetic particle processor, the cam is to engage the cam follower to rotate the rotatable hatch to a closed position.

20. A system comprising:
   a magnetic particle processor;
   a multi-well plate;
   a movable interface to automatically load the multi-well plate into the magnetic particle processor and to automatically unload the multi-well plate from the magnetic particle processor;
   a transfer device to at least one of dispense contents into or aspirate contents from the multi-well plate;
   a heater thermally coupled to the movable interface to incubate the contents in the multi-well plate;
   a resistive temperature detector to regulate a temperature of the heater;
   a cam coupled to the movable interface;
   a cam follower operatively coupled to a rotatable hatch, wherein as the movable interface moves into the magnetic particle processor, the cam is to engage the cam follower to rotate the rotatable hatch to a closed position; and a counterweight coupled to the rotatable hatch to cause the rotatable hatch to remain in an open position when the rotatable hatch opens past an approximately 45 degree angle measured from the vertical.

\* \* \* \* \*